United States Patent [19]
Casmer et al.

[11] 3,984,544
[45] Oct. 5, 1976

[54] RETINOIC ACID ESTERS OF STEROIDS OF THE PREGNANE SERIES, THEIR USE IN THE TREATMENT OF ACNE AND PHARMACEUTICAL FORMULATIONS USEFUL THEREFOR

[75] Inventors: Charles J. Casmer, Rahway; Richard W. Draper, East Orange, both of N.J.

[73] Assignee: Schering Corporation, Kenilworth, N.J.

[22] Filed: Feb. 28, 1975

[21] Appl. No.: 554,351

[52] U.S. Cl............................ 424/243; 260/239.5; 260/239.55 D; 260/397.45
[51] Int. Cl.² ........................................... C07J 5/00
[58] Field of Search.............. 260/397.45, 239.55 D, 260/239.5 R

[56] References Cited
UNITED STATES PATENTS
3,780,177    12/1973    Ercoli et al. .................. 260/397.45

*Primary Examiner*—Elbert L. Roberts
*Attorney, Agent, or Firm*—Mary S. King

[57] ABSTRACT

Novel retinoic acid esters of anti-inflammatory steroids of the pregnane series are described and their use in the treatment and control of acne vulgaris via the topical or intralesional route. A preferred mode of the invention comprises treating acne by applying topically to the affected area hydrocortisone 21-all-trans-retinoate in concentrations of from about 0.05 to about 0.15 percent. Pharmaceutical formulations and methods for the manufacture of the novel steroidal retinoates are also described.

25 Claims, No Drawings

RETINOIC ACID ESTERS OF STEROIDS OF THE PREGNANE SERIES, THEIR USE IN THE TREATMENT OF ACNE AND PHARMACEUTICAL FORMULATIONS USEFUL THEREFOR

FIELD OF THE INVENTION

This invention relates to novel compositions-of-matter, methods for their manufacture, pharmaceutical formulations thereof and the method of using said formulations in the treatment and control of acne vulgaris.

More specifically, this invention relates to novel retinoic acid esters of anti-inflammatory steroids of the pregnane series, pharmaceutical formulations thereof, and their use in the treatment and control of acne vulgaris.

In particular, this invention relates to 21-retinoates, 17α-retinoates, 16α-retinoates, 16α,21-diretinoates and 17α,21- diretinoates of 3,20-diketo-4-pregnenes and certain derivatives thereof having anti-inflammatory activity and having hydroxyl groups or hydrolyzable derivatives thereof on at least one of positions 17α and 21, to pharmaceutical formulations thereof, and their use in the treatment and control of acne vulgaris via the topical or intralesional route.

DESCRIPTION OF THE PRIOR ART

The use of retinoic acid (also known as Vitamin A acid), in particular all-trans-retinoic acid derived from Vitamin A, in the treatment of acne vulgaris via the topical route is well known in the art, being claimed in U.S. Pat. No. 3,729,568 and described in publications such as those by A. M. Kligman et al, Arch. Derm. 99, 469 (1969), by F. J. Pedace and R. Stoughton, Br. J. Derm. 84, 465 (1971) and by R. D. G. Peachey and B. L. Conner in Br. J. Derm. 85, 462(1971). From these teachings it is evident that, to be effective in reducing the number and size of comedones present in skin affected by acne, treatment with retinoic acid must be carried out at concentrations which cause visible irritation to the skin resulting in erythema followed by peeling. Because of these undesirable side effects, some patients cannot tolerate the treatment and, in some, the acne condition is made worse.

By our invention we have discovered novel retinoic acid esters of certain steroids of the pregnane series which are useful in the treatment and control of acne vulgaris when applied topically or intralesionally, being effective in reducing the number and size of comedones in skin affected by acne while advantageously being essentially non-irritating to the skin.

The foregoing is particularly surprising since we have also discovered that when a steroidan steroidal (e.g. hydrocortisone) and all-trans-retinoic acid per se are applied together topically in concentrations wherein the percentages of steroid and all-trans-retinoic acid are essentially equivalent to that present in a topical application of the corresponding steroidal retinoate (e.g. hydrocortisone 21-all-trans-retinoate), the combined application causes inflammation usually at least about equivalent to that produced by the application of retinoic acid alone, while the topical application of the steroidal retinoate (e.g. hydrocortisone 21-all-trans-retinoate) produces no significant inflammation.

DESCRIPTION OF THE COMPOSITION-OF-MATTER ASPECT OF THE INVENTION

The composition-of-matter aspect of this invention resides in the concept of a retinoic acid ester of a steroid of the pregnane series having anti-inflammatory activity and having a 20-ketone and a 3-keto-4-dehydro system or an enol ether thereof or a 3-desoxy-[3,2-c]-pyrazole derivative thereof, and also having a hydroxyl group on at least one of positions 21, 17α and 16α with the proviso that on at least one of positions 17α and 21 there is a hydroxyl group or a hydrolyzable derivative thereof; said retinoic acid ester being a member selected from the group consisting of a 21-retinoate, 17α-retinoate, 16α-retinoate, 16α,21-diretinoate and a 17α,21-diretinoate of said steroid of the pregnane series; said steroidal retinoates being useful in the treatment and control of acne while being essentially non-irritating to the skin. Preferred as anti-acne agents are the 21-all-trans-retinoate esters of said steroids of the pregnane series, particularly the 21-all-trans-retinoates of steroids having anti-inflammatory activity of about the level of activity exhibited by hydrocortisone.

Retinoic acid is known to exist in different geometric isomeric forms, the most stable and common form being all-trans-retinoic acid (also known as all-trans-Vitamin A acid) which is derived from Vitamin A (retinol). The steroidal retinoic acid esters of this invention are preferably those derived from all-trans-retinoic acid; however, also included within this invention are steroidal retinoic acid esters derived from the other isomeric forms of retinoic acid such as 11-cis-retinoic acid, 9-cis-retinoic acid, 13-cis-retinoic acid, 9,13-di-cis-retinoic acid and retro-retinoic acid. Thus, unless otherwise indicated, the terms "retinoic acid" and "retinoates" as used in the specification and claims of this application includes all the various cis and trans forms and mixtures thereof.

Typical steroidal retinoate esters of this invention useful in the treatment and control of acne include compounds which are members selected from the group consisting of a 21-retinoate, a 17α-retinoate, a 16α-retinoate, a 16α,21-deretinoate and a 17α,21-diretinoate of a member selected from the group consisting of a 3,20-diketo-4-dehydro pregnane of the following formula I:

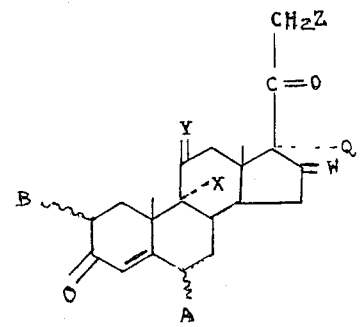

wherein A is a member selected from the group consisting of hydrogen, α-methyl, α-azido, α-bromo, α-chloro, α-fluoro, β-fluoro and α-fluoromethyl;

B is a member selected from the group consisting of hydrogen, and when Y is (H,β-OH), methyl, fluorine, chlorine and bromine;

Q is a member selected from the group consisting of hydroxy, OR wherein R is an acyl radical off a hydrocarbon-carboxylic acid having up to 12 carbon atoms, hydrogen provided W is hydrogen or (H, lower alkyl), and chlorine provided W is hydrogen or (H, lower alkyl);

W is a member selected from the group consisting of

(H, lower alkyl), (H,α-Cl), (H,α-OH), (H,α-OR₁), wherein R₁ is an acyl radical of a hydrocaboncarboxylic acid having up to 12 carbon atoms, =CHT wherein T is a member selected from the group consisting of hydrogen, lower alkyl, fluorine and chlorine, and W and Q taken together is 16α,17α-lower alkylidene-dioxy;

X is a member selected from the group consisting of hydrogen and halogen having an atomic weight of less than 100, Y is a member selected from the group consisting of oxygen provided B is hydrogen, (H,β-OH), and (H,β-halogen) provided X is halogen; and Z is a member selected from the group consisting of hydroxy; and provided Q is hydroxy, Z is also hydrogen, chlorine, fluorine, and OR₂ wherein R₂ is an acyl radical of a hydrocarboncarboxylic acid having up to 12 carbon atoms;

and the 1-dehydro, 6-dehydro and 1,6-bis-dehydro analogs thereof;

and when B is hydrogen, the 3-desoxy-[3,2-c]-pyrazole derivatives and the 6-dehydro analogs thereof;

and the 6,6-difluoro analogs of compounds of formula I wherein A is hydrogen, and the 1-dehydro analogs thereof.

Of the foregoing, preferred are the esters derived from all-trans-retinoic acid.

In the foregoing, by "lower alkyl" is contemplated hydrocarbon radicals having up to 4 carbon atoms including methyl, ethyl, iso-propyl, n-propyl, t-butyl, n-butyl, and isopropylmethyl.

The acyl radicals of the compounds of this invention as defined by R, R₁ and R₂ in Formula I hereinabove include those derived from hydrocarboncarboxylic acids having up to 12 carbon atoms which may be saturated, unsaturated, straight chain or branched chain, aliphatic, cyclic, cyclic-aliphatic, aromatic, arylaliphatic, or alkyl-aromatic, and may be substituted by alkoxy containing from 1 to 5 carbon atoms or by halogen such as fluorine, chlorine, or bromine. Typical ester groups of the steroidal retinoates of our invention are thus derived from hydrocarboncarboxylic acids such as alkanoic acids exemplified by formic, acetic, propionic, trimethylacetic, butyric, iso-butyric, valeric, iso-valeric, caproic, caprylic, capric, undecylic and lauric acids; adamantane carboxylic acids; substituted alkanoic acids such as phenoxyacetic, trifluoroacetic, and β-chloropropionic acids; aromatic and substituted aromatic acids including benzoic, toluic, p-chlorobenzoic acids; arylalkanoic acids such as phenylacetic and phenylporpionic acids; unsaturated acids such as acrylic and sorbic acids; and dibasic acids such as succinic, tartaric and phthalic acids.

Of the steroidal retinoates defined by formula I, a preferred group useful in the treatment and control of acne are members selected from the group consisting of a steroidal 21-retinoate ester, particularly a steroidal 21-all-trans-retinoate ester having the following formula II:

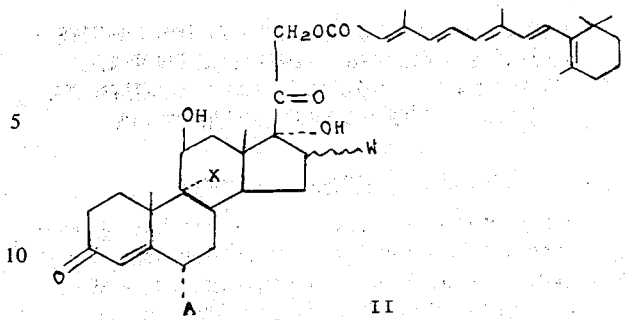

wherein A is hydrogen, methyl or fluorine; X is hydrogen or fluorine; W is hydrogen, α-methyl, β-methyl, α-hydroxy, and the 1-dehydro, 6-dehydro and 1,6-bis-dehydro analogs thereof.

Of the compounds of formula II, particularly useful esters in the treatment of acne are those wherein at least one of X and W is hydrogen.

Preferred compounds of formula II thus include steroidal retinoates such as hydrocortisone 21-all-trans-retinoate (i.e. 4-pregnene-11β,17α,21-triol-3,20-dione 21-all-trans-retinoate), the 1-dehydro analog thereof (i.e. prednisolone 21-all-trans-retinoate), the 6-dehydro analog thereof and the 1,6-bis-dehydro analog thereof (i.e. compounds of formula II wherein A, X and W are hydrogen).

Other useful esters of formula II include betamethasone 21-retinoate (i.e. 9α-fluoro-16β-methyl-1,4-pregnadiene-11β,17α,21-triol-3,20-dione 21-all-trans-retinoate) and dexamethasone 21-retinoate (i.e. 9α-fluoro-16α-methyl-1,4-pregnadiene-11β,17α,21-triol-3,20-dione 21-all-trans-retinoate), the 6-dehydro, 1(2)-dihydro, and the 1(2)-dihydro-6-dehydro analogs thereof (i.e. compounds of formula II wherein A is hydrogen, X is fluorine and W is methyl);

Triamcinolone 21-retinoate (i.e. 9α-fluoro-1,4-pregnadiene-11β,16α,17α,21-tetrol-3,20-dione 21-all-trans-retinoate) and the 6-dehydro, 1(2)-dihydro, and the 1(2)-dihydro-6-dehydro analogs thereof (i.e. compounds of formula II wherein A is hydrogen, X is fluorine and W is (H,α-OH):

6α-fluorohydrocortisone 21-all-trans-retinoate, the 1-dehydro, 6-dehydro and 1,6-bis-dehydro analogs thereof (i.e. compounds of formula II wherein A is fluorine, X and W are hydrogen); and 6α-methyl-9α-fluoro-4-pregnene-11β,17α,21-triol-3,20-dione 21-all-trans-retinoate, the 6-dehydro, 1-dehydro and the 1,6-bis-dehydro analogs thereof (i.e. compounds of formula I wherein A is methyl, X is fluorine and W is hydrogen).

Of the compounds of formula II, a preferred species is hydrocortisone 21-all-trans-retinoate.

Other steroidal 21-retinoates of this invention include 17-desoxy derivatives of formula I such as 6α-fluoro-9α-chloro-16α-methyl-1,4-pregnadiene-11β,21-diol-3,20-dione 21-all-trans-retinoate, 4-pregnene-11β,21-diol-3,20-dione 21-all-trans-retinoate and 17α-chloro-1,4-pregnadiene-11β,21-diol-3,20-dione 21-all-trans-retinoate. Also included are 21-retinoates of 17,21-diols having a hydrolyzable derivative at C-17 such as 9α-fluoro-16β-methyl-1,4-pregnadiene-11β,17α,21-triol-3,20-dione-17-n-butyrate 21-all-trans-retinoate, 6α,9α-difluoro-16α,17α-isoporpylidene- dioxy-1,4-pregnadiene-11β,21-diol-3,20 -dione 21-all-trans-retinoate and 2'-phenyl-6,16α-dimethyl-9α-fluoro-11β,17α,21trihydroxy-20-keto-4,6-pregnadieno-[3,2-c]-pyrazole 17-acetate 21-all-trans-retinoate.

In addition to 21-retinoates, the compounds of this invention include:

16α-retinoate esters such as triamcinolone 16-retinoate 21-acetate (e.g. 9α-fluoro-1,4-pregnadiene-11β,16α,17α,21-tetrol-3,20-dione 16-all-trans-retinoate 21-acetate), the 6-dehydro analog, the 1(2)-dihydro analog and the 1(2)-dihydro-6-dehydro analog thereof;

16α,21-diretinoates such as triamcinolone 16,21-diretinoate (e.g.9α-fluoro-1,4-pregnadiene-11β,16α,17α,21-tetrol-3,20-dione 16,21-di-all-trans-retinoate), the 6-dehydro analog thereof, the 1(2)-dihydro analog and the 1(2)-dihydro-6-dehydro analog thereof;

17α-retinoates of steroids of formula I such as hydrocortisone 17-all-trans-retinoate and the 1-dehydro, 6-dehydro and 1,6-bis-dehydro analogs thereof; dexamethasone 17-retinoate and betamethasone 17-retinoate (e.g. 9α-fluoro-16-methyl (α and β)- 1,4-pregnadiene-11β,17α,21-triol-3,20-dione 17-all-trans-retinoate), 9α,11β-dichloro-21-fluoro-16α-methyl-1,4-pregnadiene-17α-ol-3,20-dione 17-all-trans-retinoate, 2'-phenyl-6,16α-dimethyl-9α-fluoro-11β,17α-dihydroxy-20-keto-4,6pregnadieno-[3,2-c]- pyrazole 17-all-trans-retinoate and 9α,21-difluoro-16αmethyl-1,4-pregnadiene-11β,17α-diol-3,20-dione 17-all-trans-retinoate; and 17α,21-diretinoates of steroids of formula I such as hydrocortisone 17,21-diretinoates (e.g. 4-pregnene-11β,17α,21-triol-3,20-dione 17,21-di-all-trans-retinoate), 9α-fluoro-16α-methyl-1,4-pregnadiene-11β,17α,21-triol-3,20-dione 17,21-di-all-trans-retinoate, and 9α-fluoro-16β-methyl-1,4-pregnadiene-17α,21-diol-3,11,20-trione 17,21-di-all-trans-retinoate.

The retinoate esters of this invention, particularly the all-trans-retinoate esters as defined hereinabove including the 21-retinoate, 17α-retinoate, 16α,21-diretinoate, 17α,21-di-retinoate and preferably the 21-all-trans-retinoate esters of steroids of formula I of which a preferred group is defined by formula II, exhibit anti-acne activity when administered topically or intralesionally to the affected area while being essentially non-irritating to the skin. It is also contemplated that retinoate esters of steroid other than those specifically defined hereinabove will possess the combine properties of anti-acne activity together with no significant inflammatory activity provided the steroidal alcohol precursor is a pregnane having antiinflammatory activity (a useful level being about that exhibited by hydrocortisone) and a 20-ketone and a 3-keto-4-dehydro system or an enol ether thereof or a 3-desoxy-[3,2-c]-pyrazole derivative, and also having a hydroxyl group on at least one of positions 21, 17α and 16α providing that on at least one of positions 17α and 21 there is a hydroxyl group or a hydrolyzable derivative thereof, the retinoate ester being on at least one of positions 21, 17α and 16α.

Thus, included in the composition-of-matter aspect of this invention are steroidal retinoates useful as anti-acne agents which are not specifically defined by formula I exemplified by 6,16-dimethyl-1,4,6,15-pregnatetraene-11β,17α,21-triol-3,20-dione 21-all-trans-retinoate, 16α-methyl-1,4,8(9)-pregnatriene-11β,17α,21-triol-3,20-dione 17-propionate 21-all-trans-retinoate, 9α-fluoro-[17α,16α-d]-oxazolino-1,4-pregnadiene-11α,21-diol-3,20-dione 21-all-trans-retinoate and 3-(α-chloroethoxy)-6-formyl-9α-fluoro-16α,17α-isopropylidenedioxy-3,5-pregnadiene-11β,21-diol-20-one 21-all-trans-retinoate.

The physical embodiments of the steroidal retinoate esters of this invention are usually yellow crystalline solids which are soluble in organic solvents such as alkanols (e.g. methanol, ethanol), ethers (e.g. diethyl ether, dioxane, tetrahydrofuran) and chlorinated hydrocarbons (e.g. methylene chloride and chloroform) and are insoluble in water. Because of the presence of the five conjugated double bonds in the retinoyl radical, the steroidal retinoates of our invention are susceptible to decomposition in the presence of light, oxygen or heat. Thus, to minimize decomposition, our compounds are preferably stored in a cool place, in the dark, and under an atmosphere of an inert gas such as argon or nitrogen.

The steroidal retinoic acid esters of this invention are prepared from the corresponding steroidal alcohol via procedures utilizing techniques similar to those known in the art. Since retinoic acid is susceptible to decomposition in the presence of light, oxygen, heat or acid, all the processes of this invention are preferably carried out in the dark under an inert atmosphere (usually nitrogen). Additionally, processes carried out in an essentially neutral or alkaline medium at room temperature or lower, will usually produce higher yields of purer steroidal retinoate esters than esterifications carried out at high temperatures and/or in an acidic medium.

As indicated hereinabove, when preparing steroidal retinoate esters of this invention, the starting steroidal alcohol must be a steroid of the pregnane series having antiinflammatory activity and having a 20-ketone and a 3-keto-4-dehydro system or an enol ether thereof or a 3-desoxy-[3,2-c]-pyrazole derivative thereof, and also having a hydroxyl group on at least one of positions 21, 17α and 16α with the proviso that on at least one of positions 17α and 21 there is a hydroxyl group or a hydrolyzable derivative thereof. Thus, the starting steroid may have several free hydroxyl groups present (as in hydrocortisone-4-pregnene-11β,17α,21-triol-3,20-dione) of which some hydroxyl groups may be converted to hydrolyzable derivatives such as to lower alkanoate esters as in betamethasone 17-butyrate (9α-fluoro-16β-methyl-1,4-pregnadiene-11β,17α,21-triol-3,20-dione 17-butyrate) or as in triamcinolone 21-acetate (9α-fluoro-1,4-pregnadiene-11β,16α,17α,21-tetrol-3,20-dione 21-acetate). Another hydrolyzable derivative is an alkylidenedioxy derivative such as in 9α-fluoro-16α,17α-ethylidenedioxy-1,4-pregnadiene-11β,21-diol-3,20-dione.

The 21-retinoate esters of this invention are most conveniently prepared by the reaction of a steroidal alcohol with about an equimolar quantity of N-retinoylimidazole (prepared from retinoic acid and 1,1'-carbonyldiimidazole) in the presence of a base such as sodium methoxide, sodium amide, or imidazolylsodium and is carried out in an inert solvent (usually in an ether such as a dialkyl ether, dioxane, or preferably tetrahydrofuran), preferably in the dark and under and atmosphere of nitrogen. The esterification is conveniently carried out at room temperature, is usually completed in a short time (usually 15 to 30 minutes) as determined by thin layer chromatography, the resulting steroidal retinoate being easily isolated and purified in good yields utilizing conventional methods, usually chromatographic techniques.

Another useful method of preparing the steroidal 21-retinoates comprises the reaction of the steroidal alcohol with approximately equimolar quantities of retinoic acid and of a carbodiimide in an inert solvent including acetonitrile, chlorinated hydrocarbons (e.g. methylene chloride) and ethers (e.g. dioxane and preferably tetrahydrofuran). Carbodiimides useful in this process include dicyclohexylcarbodiimide and 1-cyclohexyl-3-(2-morpholinoethyl)carbodiimide metho-p-toluenesulfonate. This process is usually carried out in the dark under an atmosphere of nitrogen at room temperature for long periods of time during which additional equimolar portions of retinoic acid and carbodiimide are added. The reaction is continued until thin layer chromatography of an aliquot of the reaction mixture indicates most of the steroidal alcohol has been converted (which usually requires at least two days reaction time). Isolation and purification of the resultant steroidal 21-retinoate is easily effected utilizing extraction methods followed by chromatographic techniques.

The steroidal 21-retinoates of this invention may also be prepared via more conventional methods such as (1) reaction of the steroidal alcohol in a base (e.g. pyridine) with retinoyl chloride, (2) reaction of the steroidal alcohol with retinoic acid in the presence of ethoxyacetylene in an inert solvent (e.g. ethyl acetate), (3) reaction of the steroidal alcohol and retinoic acid in the presence of a catalytic quantity of boron trifluoride etherate in an inert solvent (e.g. ether), and (4) reaction of the steroidal alcohol with N-hydroxy-phthalimide retinoate or N-hydroxy-succinimide retinoate, saaid reagents being prepared from retinoic acid and N-hydroxy-phthalimide (or succinimide) in the presence of a carbodiimide.

In the foregoing and other processes disclosed in this specification, by "inert solvent" is meant a solvent in which the steroidal alcohol and reagents are soluble and which will not react with the reagents so there is produced a minimum of competing side reactions.

The steroidal 17-mono-retinoate esters of $17\alpha,21$-dihydroxy-20-keto steroids are most conveniently made from the corresponding 21-mono-retinoate utilizing known procedures. Thus, for example, a $17\alpha,21$-dihydroxy-20-keto-steroidal 21-retinoate upon reaction with a non-hydroxylic base in an aprotic anhydrous medium (e.g. with lithium dimethyl cuprate in anhydrous tetrahydrofuran) followed by protonation of the reaction mixture (such as with ammonium chloride) yields the corresponding steroidal 17-retinoate which is conveniently isolated by extraction with an organic solvent (e.g. ethyl acetate) and purified via chromatographic techniques. This reaction is carried out at low temperatures, i.e. at about $-40°C$, preferably in the dark under nitrogen.

When preparing 17-mono-retinoates of steroids having a $17\alpha$-hydroxy-20-keto-21-desoxy system, any 11- and/or 16-hydroxyl groups present are first protected by preparing the 11- and/or 16-trifluoroacetates such as by esterification with trifluoroacetic anhydride in pyridine. The 17-monoretinoate is then prepared by reaction of the $17\alpha$-hydroxy-21-desoxy-20-keto steroid with retinoic acid chloride in the presence of dimethylaminopyridine in pyridine or by reaction with retinoic acid and trifluoroacetic anhydride in the presence of p-toluenesulfonic acid. The resulting 17-monoretinoate esters are then isolated, any remaining protecting 11- and/or 16-trifluoroacetyl groups removed, and the 17-retinoate-21-desoxy steroid is purified utilizing methods known in the art such as those described in Example 8.

Alternatively, $17\alpha$-retinoate esters of 20-keto-21-desoxy steroids are prepared from the corresponding $17\alpha$-retinoate esters of 20-keto-$17\alpha,21$-dihydroxy steroids utilizing conventional techniques such as illustrated in Example 9 whereby a 17-mono-retinoate of a 21-hydroxy steroid (e.g. dexamethasone 17-all-trans-retinoate) upon treatment with methanesulfonyl chloride in pyridine is converted to the corresponding steroidal 17-retinoate 21-methanesulfonate (e.g. dexamethasone 17-all-trans-retinoate 21-methanesulfonate), which, in turn, upon treatment with sodium iodide in dimethylformamide in the presence of acetic acid yields an unsubstituted 21-desoxy 17-retinoate of the invention (e.g. $9\alpha$-fluoro-$16\alpha$-methyl-1,4-pregnadiene-$11\beta,17\alpha$-diol-3,20-dione 17-all-trans-retinoate.). Alternatively, treatment of the 17-retinoate 21-methanesulfonate intermediate with lithium chloride or lithium fluoride yields the corresponding 17-retinoate 21-desoxy-21-halogeno derivative, e.g. $9\alpha$-fluoro-$16\alpha$-methyl-21-chloro-1,4-pregnadiene-$11\beta,17\alpha$-diol-3,20-dione 17-all-trans-retinoate or $9\alpha,21$-difluoro-$16\alpha$-methyl-1,4-pregnadiene-$11\beta,17\alpha$-diol-3,20-dione 17-all-trans-retinoate, respectively.

The steroidal 17,21-diretinoate esters of this invention may be prepared from the corresponding $17\alpha$-retinoyloxy-21-hydroxy steroid via any of the procedures discussed hereinabove for preparing 21-retinoate esters, a preferred method being the reaction of the $17\alpha$-retinoyloxy-21-hydroxy steroid with N-retinoylimidazole in the presence of a base, such as illustrated in Example 6.

Alternatively, after protecting any $11\beta$- and/or $16\alpha$-hydroxy groups by conversion thereof to their trifluoroacetate esters, the $17\alpha,21$-diretinoates may be prepared utilizing techniques analogous to known techniques such as by reaction of the $17\alpha,21$-dihydroxy-20-keto-4-pregnene with at least two moles of retinoic acid in the presence of trifluoroacetic anhydride and p-toluenesulfonic acid or by reaction with at least two moles of retinoyl chloride in pyridine in the presence of dimethylaminopyridine.

The steroidal $16\alpha,21$-diretionate esters of this invention are most conveniently prepared by reacting a $16\alpha,17\alpha,21$-trihydroxy-20-keto-4-pregnene with about two moles of N-retinoylimidazole in the presence of a base such as sodium methoxide or imidazolylsodium or by reaction with about two moles of retinoic acid in the presence of a carbodiimide.

THE METHOD-OF-USE AND PHARMACEUTICAL COMPOSITION ASPECTS OF THE INVENTION

The 21-retinoate, $17\alpha$-retinoate, $16\alpha$-retinoate, $16\alpha,21$-diretinoate and the $17\alpha,21$-diretinoate esters of anti-inflammatory steroids of the pregnane series (particularly those having an order of anti-inflammatory activity about that exhibited by hydrocortisone) and having a 20-keto and a 3-keto-4-dehydro system or an enol ether thereof or a 3-desoxy-[3,2-c]-pyrazole derivative thereof, and also having a hydroxyl group on at least one of positions 21, $17\alpha$ and $16\alpha$ with the proviso that on at least one of positions $17\alpha$ and 21 there is a hydroxyl group or a hydrolyzable derivative thereof, such as those defined by formulae I and II hereinabove, are novel compounds which have been found to possess anti-acne activity with no significant concomitant inflammatory activity as evidenced by tests in the rhino variant hairless mouse. When applied topically to the skin of these mice which have comedone-like lesions, the steroidal retinoates of our invention (e.g. the steroidal all-trans-retinoates) reduce the size and number of comedones, while advantageously causing little or no irritation to the skin such as is caused by the topical application of retinoic acid per se. That our steroidal retinoates are effective topically in reducing the number of comedones while advantageously causing no significant inflammatory response of the skin is all the more surprising and unexpected in view of our further discovery that when all-trans-retinoic acid and a steroid having anti-inflammatory activity, e.g. of a level such as exhibited by hydrocortisone or prednisolone are applied together topically to skin affected by acne-like lesions (e.g. as in the rhino variant hairless mouse) in molecular equivalent amounts to a given quantity of the corresponding steroidal retinoate (e.g. hydrocortisone 21-all-trans-retinoate) the combined steroid and all-trans-retinoic acid application produces a substantial inflammatory response which is sometimes even greater than that produced by all-trans-retinoic acid alone. We have also discovered that the combined properties of anti-acne activity with minimal inflammatory response is unique to the steroidal retinoic acid esters of our invention since such activity is not exhibited by other steroidal esters such as steroidal lower alkanoic acid esters (e.g. hydrocortisone 21-acetate) or steroidal esters of acids having a similar lypophilicity as retinoic acid, e.g. of esters such as hydrocortisone 21-stearate. Moreover, retinoic acid esters of non-steroidal alcohols having the same lypophilicity of hydrocortisone 21-retinoate (e.g. 2-phenylethyl retinoate) were found ineffective when applied topically to skin affected by acne-like lesions.

The anti-acne properties of the steroidal retinoates of this invention are demonstrated by tests in the rhino variant hairless mouse, an animal model found useful in screening drugs for comedolytic properties. In these tests, a solution of a steroidal retinoate ester of this invention (e.g. hydrocortisone 21-all-trans-retinoate) in an inert solvent (e.g. acetone) in concentrations ranging from 0.01 percent to about 0.5 percent, usually at about 0.1 percent concentration, is applied topically to the skin of a rhino variant hairless mouse once a day for six days. The area of the pilary canal containing keratin (comedo), the number of acute inflammatory cells, as well as the epidermal thickness are measured before and after treatment. Areas treaded with a solution of a steroidal retinoate of this invention were compared with areas treated with solvent alone, with areas treated with a solution of all-trans-retinoic acid, with areas treated with a solution of the free steroidal alcohol (e.g. hydrocortisone), and with areas treated with all-trans-retinoic acid together with a steroidal alcohol. In general, it was discovered that the steroidal retinoates of this invention significantly reduced both the area of the pilary canal and the amount of keratin contained therein without significant inflammation when compared with areas treated by solvent alone; that application of retinoic acid in the same solvent either alone or together with the steroidal alcohol precursor of the steroidal retinoate being tested, reduced the size of pilary canal but also caused a significant increase in the inflammatory cells present in the treated skin. It was discovered also that treatment with the steroidal alcohol alone had no significant effect on the pilary canal, usually slightly increasing the size thereof.

A preferred compound of this invention is hydrocortisone 21-all-trans-retinoate which, when applied topically in a 0.1 percent solution for six days, is as effective in reducing comedones as a 0.02 percent all-trans-retinoic acid solution applied over the same period, while not causing any of the inflammatory side effects exhibited by the retinoic acid solutions.

In view of the comedolytic activity of the steroidal retinoates, our invention includes the concept of the method of treating and controlling acne which comprises applying either topically or intralesionally to the affected area in a concentration effective for the treatment of acne, a steroidal retinoate ester of this invention as defined hereinabove, together with a non-toxic, pharmaceutically acceptable carrier.

The method-of-treating and controlling acne of this invention is preferably carried out via the topical route utilizing steroidal all-trans-retinoate esters.

When carrying out our method, a composition comprising a steroidal retinoate (preferably a steroidal all-trans-retinoate) together with a non-toxic, pharmaceutically acceptable carrier, usually at concentrations in the range of from about 0.01 percent to about 0.5 percent, preferably from about 0.025 to about 0.1 percent, is applied once or twice daily to skin affected by acne vulgaris usually via the topical route (although intralesional injections may be made in cases of severe acne) until the acne condition has improved. Topical applications of the steroidal retinoates may then be continued at less frequent intervals (e.g. every other day) to control comedone formation in order to prevent return of severe acne conditions.

The steroidal retinoates are conveniently applied in a liquid solvent, preferably in a water-miscible liquid carrier made up of hydrophylic liquids having a high solvating action, e.g. a solution of a steroidal retinoate in ethyl alcohol together with polyethyleneglycol. In general, the steroidal retinoates may be applied in any topical form including creams, lotions, aerosols and ointments which are prepared by combining the active ingredient, e.g. a steroidal retinoate such as defined by formula I, with conventional pharmaceutical diluents and carriers used in topical formulations comprising steroids.

Thus, the pharmaceutical composition aspect of this invention resides in the concept of a pharmaceutical composition comprising an anti-acne effective amount of a compound selected from the group consisting of a 21-retinoate, a 17α-retinoate, a 16α-retinoate, a 16α,21-diretinoate, and a 17α,21-diretinoate of a steroid of the pregnane series, said steroid having anti-inflammatory activity and having a 20-ketone and a 3-keto-4-dehydro system or an enol ether thereof or a 3-desoxy-[3,2-c]-pyrazole derivative thereof, and also having a hydroxyl group on at least one of positions 21, 17α and 16α with the proviso that on at least one of positions 17α and 21 there is a hydroxyl group or a hydrolyzable derivative thereof, together with a non-toxic, pharmaceutically acceptable carrier.

Preferred are topical compositions comprising steroidal all-trans-retinoate esters, particularly those defined by formula II hereinabove wherein at least one of X and W is hydrogen; compositions comprising hydrocortisone 21-all-trans-retinoate being particularly valuable.

The pharmaceutical compositions of the invention are made according to known procedures, some of which are described in detail in Examples 14 and 15 hereinbelow.

The following are examples to illustrate the invention, it being understood the invention is not to be limited thereby.

In following Examples 1–15, the retinoic acid used as reagent is all-trans-retinoic acid and the retinoic acid esters prepared thereby and named in Examples 1–15 are all-trans-retinoate esters. In the following examples, by substituting for all-trans-retinoic acid other isomeric forms thereof, such as 11-cis-retinoic acid, 9-cisretinoic acid, 13-cis-retinoic acid, retro-retinoic acid, and 9,13-di-cis-retinoic acid, there is obtained the corresponding isomeric ester, e.g. the 11-cis-retinoate, 9-cis-retinoate, 13-cis-retinoate, retro-retinoate, and the 9,13-di-cis-retinoate, respectively.

EXAMPLE 1

9α-FLUORO-11-OXYGENATED-16-METHYL-1,4-PREGNADIENE-17α,21-DIOL-3,20-DIONE 21-RETINOATES

A. 1. To a solution of N-retinoylimidazole (350 mg., 1 mmole) and 9α-fluoro-16α-methyl-1,4-pregnadiene-11β,17α,21-triol-3,20-dione (392 mg., 1 mmole) in dry tetrahydrofuran (25 ml.) under nitrogen in the dark add sodium methoxide (28 mg., 0.5 mmoles). Stir at room temperature for 15 minutes, evaporate the reaction mixture in vacuo and chromatograph the resultant residue over a silica gel column eluting first with petroleum ether and then with petroleum ether/ether solvent mixtures containing increasing amounts of ether, and finally eluting with ether. Combine the like fractions as determined by thin layer chromatography and evaporate to a residue comprising 9α-fluoro-16α-methyl-1,4-pregnadiene-11β,17α,21-triol-3,20-dione 21-retinoate. Purify by crystallizing from ether/petroleum ether, yield 230 mg.; m.p. 130°–132°C; $[\alpha]_D^{26}$ + 215° (chloroform); mass spectrum M$^+$ = 674; $\lambda_{max}^{methanol}$ ; 242 nm ($\epsilon$=20,000), 358 nm ($\epsilon$=33,000).

2. In similar manner treat each of the following with N-retinoylimidazole and sodium methoxide in tetrahydrofuran under nitrogen in the dark.
   1. 9α-fluoro-16α-methyl-1,4-pregnadiene-17α,21-diol-3,11,20-trione,
   2. 9α-fluoro-16α-methyl-1,4-pregnadiene-11β,17α,21-triol-3,20-dione,
   3. 9α-fluoro-16β-methyl-1,4-pregnadiene-17α,21-diol-3,11,20-trione. Isolate and purify each of the resultant products in a manner similar to that described hereinabove to obtain, respectively,
      1. 9α-fluoro-16α-methyl-1,4-pregnadiene-17α,21-diol-3,11,20- trione 21-retinoate,
      2. 9α-fluoro-16β-methyl-1,4-pregnadiene-11β,17α,21-triol-3,20-dione 21-retinoate,
      3. 9α-fluoro-16β-methyl-1,4-pregnadiene-17α,21-diol-3,11,20-trione 21-retinoate.

B. 1. Alternatively, the compound of Example 1A(1) is prepared as follows.

To a suspension of 9α-fluoro-16α-methyl-1,4-pregnadiene-11β,17α,21-triol-3,20-dione (392 mg., 1 mmole) in methylene chloride (50 ml.) under nitrogen and in the dark, add retinoic acid (300 mg., 1 mmole) and 1-cyclohexyl-3-(2-morpholinoethyl)-carbodiimide metho-p-toluenesulfonate (424 mg., 1 mmole). Stir at room temperature for 17 hours, then add an additional mmole of retinoic acid and an additional mmole of the diimide. and continue stirring the reaction mixture for an additional 24 hours. Extract the reaction mixture sequentially with 2 percent hydrochloric acid, water, 5 percent aqueous sodium bicarbonate and again with water. Dry over sodium sulfate and evaporate in vacuo. Chromatograph the resultant residue on silica gel FG thick layer plates eluting with ethyl acetate/chloroform (1:2). Remove the steroidal retinoate band from the thick layer plate, extract with ethyl acetate and evaporate in vacuo to a residue comprising 9α-fluoro-16α-methyl-1,4-pregnadiene-11β,17α,21-triol-3,20-dione 21-retinoate. Purify by crystallization from ether/petroleum ether, yield 128 mg. having physical constants identical to those of the compound prepared in Example 1-A.

EXAMPLE 2

11-OXYGENATED-1,4-PREGNADIENE-17α,21-DIOL-3,20-DIONE 21-RETINOATES

A. To a suspension of 1,4-pregnadiene-11β,17α,21-triol-3,20-dione (360 mg., 1 mmole) in dry acetonitrile (50 ml.) under nitrogen and in the dark, add 1-cyclohexyl-3-(2-morpholinoethyl)-carbodiimide metho-p-toluenesulfonate (424 mg., 1 mmole) and retinoic acid (300 mg., 1 mmole). Stir the reaction mixture for 5 days during which time add at intervals three 1 mmole portions each of retinoic acid and of the diimide. Pour the reaction mixture into 2 percent hydrochloric acid, filter off and dry the resultant precipitate. Rinse the dried precipitate with a small portion of cold ethyl acetate and chromatograph on silica gel GF thick layer plates eluting with chloroform/ethyl acetate (1:1). Scrape off the steroidal retinoate band and extract with ethyl acetate. Evaporate the extract in vacuo to a residue comprising 1,4-pregnadiene-11β,17α, 21-triol-3,20-dione 21-retinoate. Purify by crystallization from ether, yield 138 mg.; m.p. 216–218°C; $[\alpha]_D^{26}$ = 252° (chloroform); mass spectrum: M$^+$642; $\lambda_{max}^{methanol}$ 242 nm ($\epsilon$=19,600), 357 nm ($\epsilon$=32,000).

B. In similar manner treat 1,4-pregnadiene-17α,21-diol-3,11,20-trione in acetonitrile under nitrogen in the dark with retinoic acid and 1-cyclohexyl-3-(2-morpholinoethyl)-carbodiimide metho-p-toluenesulfonate to obtain 1,4-pregnadiene-17α,21-diol-3,11,20-trione 21-retinoate.

C. Alternatively, the 21-retinoates of this example are prepared from the corresponding steroidal 21-hydroxy compound by treatment with N-retinoylimidazole and sodium methoxide in tetrahydrofuran according to the procedure of Example 1-A.

EXAMPLE 3

11-OXYGENATED-4-PREGNENE-17α,21-DIOL-3,20-DIONE-21-RETINOATES

A. 1. To a solution of 4-pregnene-11β,17α,21-triol-3,20-dione (362 mg., 1 mmole) in methylene chloride (100 ml.) add retinoic acid (300 mg., 1 mmole) and 1-cyclohexyl-3-(2-morpholinoethyl)-carbodiimide metho-p-toluenesulfonate (424 mg., 1 mmole). Stir under an atmosphere of nitrogen in the dark at room temperature for 15 hours. Add 4 additional 1 mmole portions each of retinoic acid and the diimide at 24 hour intervals, after which time no starting steroid remains as determined by thin layer chromatography. Filter the reaction mixture, evaporate the filtrate in vacuo, and chromatograph the resultant residue on silica gel GF plates eluting with ethyl acetate/petroleum ether (1:1). Remove the steroidal retinoate band and extract with ethyl acetate, then evaporate the ethyl acetate extracts in vacuo to a residue comprising 4-pregnene-11β,17α,21-triol-3,20-dione 21-retinoate. Purify by crystallization from isopropyl ether/petroleum ether, yield 276 mg.; m.p. 218–220°C; $[\alpha]_D^{26}$ + 151.2° (chloroform); mass spectrum M$^+$= 644, $\lambda_{max}^{methanol}$; 242 nm ($\epsilon$=21,500) and 357 ($\epsilon$=42,600).

2. Alternatively, the compound of this example is prepared by treating 4-pregnene-11β,17α,21-triol-3,20-dione with N-retinoylimidazole and sodium methoxide in tetrahydrofuran under an atmosphere of nitrogen in the manner described in Example 1-A.

B. In a manner similar to that described in Example 2A treat 4-pregnene-17α,21-diol-3,11,20-trione with retinoic acid and 1-cyclohexyl-3-(2-morpholinoethyl)-carbodiimide metho-p-toluenesulfonate in methylene chloride in the dark. Isolate and purify the resultant product in a manner similar to that described to obtain 4-pregnene-17α,21-diol-3,11,20-trione-21-retinoate.

EXAMPLE 4

9α-FLUORO-16-METHYL-1,4-PREGNADIENE-11β,17α,21-TRIOL-3,20-DIONE-17-LOWER ALKANOATE 21-RETINOATES

A. 9α-Fluoro-16β-Methyl-1,4-Pregnadiene-11β,17α,21-Triol-3,20-Dione 17-Valerate 21-Retinoate.

1. To a solution of 9α-fluoro-16β-methyl-1,4-pregnadiene-11β, 17α,21-triol-3,20-dione 17-valerate (1.59 gm.) in methylene chloride (250 ml.) under an atmosphere of nitrogen at room temperature add 1-cyclohexyl-3-(2-morpholinoethyl)-carbodiimide metho-p-toluenesulfonate (1.4 gm.) and retinoic acid (1 gm.). Stir the reaction mixture under an atmosphere of nitrogen in the dark for 14 hours, then add an additional 1.4 gm. of the diimide and 1 gm. of retinoic acid. Stir an additional 24 hours in the dark. Extract the reaction mixture with dilute hydrochloric acid (5 percent), then with water. Dry the methylene chloride solution over magnesium sulfate, evaporate in vacuo and chromatograph the resultant residue on silica gel GF thick layer plates eluting with petroleum ether-/ethyl acetate (2:1). Scrape off the steroidal retinoate band and extract with ethyl acetate. Evaporate the combined ethyl acetate extracts in vacuo to a residue comprising 9α-fluoro-16β-methyl-1,4-pregnadiene-11β, 17α,21-triol-3,20-dione 17-valerate 21-retinoate. Purify by crystallization from isopropyl ether/hexane to give 1.1 gm. of purified 9α-fluoro-16β-methyl-1,4-pregnadiene-11β,17α,21-triol-3,20-dione 17-valerate 21-retinoate; m.p. 118–120°C; $[\alpha]_D^{26}$ + 175.1° (chloroform); mass spectrum: $M^+$758; $\lambda_{max}^{methanol}$ 250 nm ($\epsilon$=24,900), 365 ($\epsilon$=29,400).

2. In a manner similar to that described in Example 4A treat 9α-fluoro-16α-methyl-1,4-pregnadiene-11β,17α,21-triol-3,20-dione-17-valerate with retinoic acid and 1-cyclohexyl-3-(2-morpholinoethyl)-carbodiimide metho-p-toluenesulfonate in methylene chloride at room temperature in the dark under an atmosphere of nitrogen. Isolate and purify the resultant product in a manner similar to that described to obtain 9α-16α-methyl-1,4-pregnadiene-11β,17α,21-triol-3,20-dione 17-valerate 21-retinoate.

B. In a manner similar to that described in Example 4A treat each of the following steroids with retinoic acid and the diimide in methylene chloride under an atmosphere of nitrogen in the dark:

1. 9α-fluoro-16β-methyl-1,4-pregnadiene-11β,17α,21-triol-3,20-dione 17-propionate,
2. 9α-fluoro-16β-methyl-1,4-pregnadiene-11β,17α,21-triol-3,20-dione 17-n-butyrate,
3. 9α-fluoro-16α-methyl-1,4-pregnadiene-11β,17α,21-triol-3,20-dione 17-propionate,
4. 9α-fluoro-16α-methyl-1,4-pregnadiene-11β,17α,21-triol-3,20-dione 17-n-butyrate. Isolate and purify each of the resultant products in a manner similar to that described in Example 4A to obtain, respectively,

1. 9α-fluoro-16β-methyl-1,4-pregnadiene-11β,17α,21-triol-3,20-dione 17-propionate 21-retinoate,
2. 9α-fluoro-16β-methyl-1,4-pregnadiene-11β,17α,21-triol-3,20 -dione 17-n-butyrate 21-retinoate,
3. 9α-fluoro-16α-methyl-1,4-pregnadiene-11β,17α,21-triol-3,20-dione 17-propionate 21-retinoate,
4. 9α-fluoro-16α-methyl-1,4-pregnadiene-11β,17α,21-triol-3,20-dione 17-n-butyrate 21-retinoate.

EXAMPLE 5

11-OXYGENATED-4-PREGNENE-17α,21-DIOL-3,20-DIONE 17-RETINOATES AND 9α-FLUORO-16-METHYL-1-DEHYDRO ANALOGS THEREOF

A. 4-Pregnene-11β,17α,21-Triol-3,20-Dione 17-Retinoate.

To a suspension of cuprous iodide (100 mg.) in dry tetrahydrofuran (1 ml.) in the dark under an atmosphere of nitrogen at 0°C add methyl lithium solution in ether (0.3 ml., 1.8 M). Stir the mixture for 15 minutes, then lower the temperature to −40°C and add a solution of 4-pregnene-11β,17α,21-triol-3,20-dione 21-retinoate (32 mg., 0.05 mmoles) in dry tetrahydrofuran (1 ml.). Allow the resulting mixture to stir for 50 minutes in the dark at −40°C under an atmosphere of nitrogen, then pour the reaction mixture into aqueous ammonium chloride and shake well. Extract the reaction mixture with ethyl acetate, wash the combined ethyl acetate extracts with water, then dry over magnesium sulfate, and evaporate in vacuo to a residue comprising 4-pregnene-11β,17α,21-triol-3,20-dione 17-retinoate. Purify by chromatographing on silica gel GF preparative plates eluting with chloroform/ethyl acetate (3:1). Scrape off the most polar steroidal retinoate band and extract the band with ethyl acetate to obtain 22 mg. of 4-pregnene-11β,17α,21-triol-3,20-dione 17-retinoate; mass spectrum $M^+$= 644.

B. 4-Pregnene-17α,21-Diol-3,11,20-Trione 17-Retinoate.

In a manner similar to that described in Example 5A treat 4-pregnene-17α,21-diol-3,11,20-trione 21-retinoate with cuprous iodide and methyl lithium in dry tetrahydrofuran and then isolate and purify the resultant product in the described manner to obtain 4-pregnene-17α,21-diol-3,11,20-trione 17-retinoate.

9α-Fluoro-16-Methyl-1,4-Pregnadiene-11β,17α,21-Triol-3,20-Dione 17-Retinoate.

1. To a suspension of cuprous iodide (560 mg.) in dry tetrahydrofuran (5.6 ml.) in the dark under an atmosphere of nitrogen at 0°C add methyl lithium solution in ether (1.7 ml., 1.8 M). Allow the mixture to stir at 0°C in the dark under an atmosphere of nitrogen for 15 minutes, then lower the temperature to −40°C and add a solution of 9α-fluoro-16α-methyl-1,4-pregnadiene-11β,17α,21-triol-3,20-dione 21-retinoate (190 mg.) in dry tetrahydrofuran (5.6 ml.). Allow the resulting mixture to stir at −40°C in the dark under an atmosphere of nitrogen for 20 minutes, then pour into aqueous ammonium chloride and shake well. Extract with ethyl acetate, wash the combined extracts with water, then dry over magnesium sulfate and evaporate the solvent in vacuo to a residue comprising 9α-fluoro-16α-methyl-1,4-pregnadiene-11β,17α,21-triol-3,20-dione 17-retinoate. Purify by chromatographing on silica gel GF preparative plates eluting with chloroform/ethyl acetate (3:1). Remove the most polar steroidal retinoate band, then extract the retinoate band with ethyl acetate. Evaporate the combined extracts in vacuo to a residue followed by crystallization of the residue from ether/petroleum ether to obtain 9α-fluoro-16α-methyl-1,4-pregnadiene-11β,17α,21-triol-3,20-dione 17-retinoate, yield 37 mg.

2. In a manner similar to that described in Example 5C (1) treat 9α-fluoro-16β-methyl-1,4-pregnadiene-11β,17α,21-triol-3,20-dione 21-retinoate with cuprous iodide and methyl lithium solution at −40°C under an atmosphere of nitrogen and in the dark. Isolate and purify the resultant product in a manner similar to that described to obtain 9α-fluoro-16β-methyl-1,4-pregnadiene-11β,17α,21-triol-3,20-dione 17-retinoate.

D. 9α-Fluoro-16-Methyl-1,4-Pregnadiene-17α,21-Diol-3,11,20-Trione 17-Retinoates.

In a manner similar to that described in Example 5C (1) treat each of 9α-fluoro16α-methyl-1,4-pregnadiene-17α,21-diol-3,11,20-trione 21-retinoate and 9α-fluoro-16β-methyl-1,4-pregnadiene-17α,21-diol-3,11,20-trione 21-retinoate with cuprous iodide and methyl lithium in tetrahydrofuran in the dark under an atmosphere of nitrogen at −40°C. Isolate and purify each of the resultant products in a manner similar to that described to obtain 9α-fluoro-16α-methyl-1,4-pregnadiene-17α,21-diol-3,11,20-trione 17-retinoate and 9α-fluoro-16β-methyl-1,4-pregnadiene-17α,21-diol-3,11,20-trione 17-retinoate, respectively.

EXAMPLE 6

11-OXYGENATED-4-PREGNENE-17α,21-DIOL-3,20-DIONE-17,21-DIRETINOATES AND THE 11-OXYGENATED-16-METHYL-9α-FLUORO-1,4-PREGNADIENE-17α,21-DIOL-3,20-DIONE 17,21-DIRETINOATES

A. 4-Pregnene-11β,17α,21-Triol-3,20-Dione 17,21-Diretinoate.

In a manner similar to that described in Example 1-A, to a solution of N-retinoylimidazole (350 mg., 1 mmole) and 4-pregnene-11β,17α,21-triol-3,20-dione 17-retinoate (644 mg., 1 mmole) in dry tetrahydrofuran under nitrogen in the dark add sodium methoxide (25 mg., 0.5 mmoles). Stir at room temperature for 15 minutes, then evaporate the reaction mixture in vacuo and chromatgraph the resultant residue on a silica gel column eluting first with petroleum ether and then with petroleum ether/ether solvent mixtures containing increasing amounts of ether and finally eluting with ether. Combine the like fractions as determined by this layer chromatography and evaporate to a residue comprising 4-pregnene-11β,17α,21-dione-17,21-diretinoate, yield 550 mg. Purify by crystallizing from ether/petroleum ether.

B. 4-Pregnene-17α,21-Diol-3,11,20-Trione 17,21-Diretinoate.

In a manner similar to that described in above Example 6A treat 4-pregnene-17α,21-diol-3,11,20-trione 17-retinoate with N-retinoylimidazole and sodium methoxide under an atmosphere of nitrogen in the dark. Isolate and purify the resultant product in a manner similar to that described to obtain 4-pregnene-17α,21-diol-3,11,20-trione 17,21-diretinoate.

C. 9α-Fluoro-16α-Methyl-1,4-Pregnadiene-11β,17α,21-Triol-3,20-Dione 17,21-Diretionoate.

To a solution of N-retinoylimidazole (175 mg., 0.5 mmoles) and 9α-fluoro-16α-methyl-1,4-pregnadiene-11β,17α,21-triol-3,20-dione 17-retinoate (337 mg., 0.5 mmoles) in dry tetrahydrofuran (25 ml.) under nitrogen in the dark add sodium methoxide (14 mg., 0.25 mmoles). Stir at room temperature for 15 minutes, evaporate the reaction mixture in vacuo and chromatograph the resultant residue on a silica gel column eluting first with petroleum ether, then with petroleum ether/ether solvent mixtures containing increasing amounts of ether and finally eluting with ether. Combine the like fractions as determined by thin layer chromatography and evaporate the combined eluates to a residue comprising 9α-fluoro-16α-methyl-1,4-pregnadiene-11β,17α,21-triol-3,20-dione 17,21-diretinoate, yield 251 mg. Purify by crystallizing from ether/petroleum ether.

D. In a manner similar to that described in Example 6C treat each of the following with N-retinoylimidazole and sodium methoxide in dry tetrahydrofuan under an atmosphere of nitrogen and in the dark.

1. 9α-fluoro-16β-methyl-1,4-pregnadiene-11β,17α,21-triol-3,20-dione 17-retinoate,
2. 9α-fluoro-16β-methyl-1,4-pregnadiene-17α,21-diol-3,11,20-trione 17-retinoate, and
3. 9α-fluoro-16α-methyl-1,4-pregnadiene-17α,21-diol-3,11,20-trione 17-retinoate. Isolate and purify each of the resultant products in a manner similar to that described to obtain, respectively,
1. 9α-fluoro-16β-methyl-1,4-pregnadiene-11β,17α,21-triol-3,20-dione 17,21-diretinoate,
2. 9α-fluoro-16β methyl-1,4-pregnadiene-17α,21-diol-3,11,20-trione 17,21-diretinoate, and
3. 9α-fluoro-16α-methyl-1,4-pregnadiene-17α,21-diol-3,11,20-trione 17,21-diretinoate.

EXAMPLE 7

THE 16-RETINOATE-21-ACETATE AND THE 16,21-DIRETINOATES OF 9α-FLUORO-1,4-PREGNADIENE-11β,16α,17α,21-TETROL-3,20-DIONE

A. 9α-Fluoro-1,4-pregnadiene-11β,16α,17α,21-Tetrol-3,30-Dione 16-Retinoate-21-Acetate.

To a solution of 9α-fluoro-1,4-pregnadiene-11β,16α,17α,21-tetrol-3,20-dione 21-acetate (22.5 mg., 0.05 mmoles) and N-retinoylimidazole (17.5 mg., 0.05 mmoles) in dry tetrahydrofuran (2 ml.) under an atmosphere of nitrogen and in the dark add sodium methoxide (2.8 mg., 0.05 mmoles). Stir the mixture in the dark under nitrogen for 2 hours, remove the solvent in vacuo and chromatograph the resultant residue on silica gel GF preparative plates eluting with chloroform/ethyl acetate (3:1). Remove the steroidal retinoate band from the preparative plate and extract with ethyl acetate, then evaporate the ethyl acetate solution in vacuo to a residue comprising 9α-fluoro-1,4-pregnadiene-11β,16α,17α,21-tetrol-3,20-dione 16-retinoate-21-acetate; $M^+$ 718 $\lambda_{max}^{MeOH}$ 237 nm ($\epsilon$=20,500) and 357 ($\epsilon$=32,000).

B. 9α-Fluoro-1,4-Pregnadiene-11β,16α,17α,21-Tetrol-3,20-Dione 16,21-Diretinoate.

In a manner similar to that described in Example 7A treat 9α-fluoro-1,4-pregnadiene-11β,16α,17α,21-tetrol-3,20-dione (41 mg., 0.1 mmoles) and N-retinoylimidazole (70 mg. 0.2 mmoles) in dry tetrahydrofuran (5 ml.) in the dark under an atmosphere of nitrogen and at room temperature with sodium methoxide (5.6 mg., 0.1 mmoles). Stir for 2 hours at room temperature in the dark under an atmosphere of nitrogen, evaporate the solvent in vacuo and chromatograph the resultant residue on silica gel preparative GF plates eluting with chloroform/ethyl acetate (3:1). Remove the less polar steroidal diretinoate band and extract with ethyl acetate. Evaporate the combined ethyl acetate extract in vacuo to a residue comprising 9α-fluoro-1,4-pregnadiene-11β,16α,17α,21-tetrol-3,20-dione 16,21-diretinoate.

EXAMPLE 8

9α-FLUORO-21-CHLORO-16α-METHYL-1,4-PREGNADIENE-11β,17α-DIOL-3,20-DIONE 17-RETINOATE

A. 9α-Fluoro-21-Chloro-16α-Methyl-1,4-Pregnadiene-11β,17α-Diol-3,20-Dione 11-Trifluoroacetate.

To a solution of 9α-fluoro-21-chloro-16α-methyl-1,4-pregnadiene-11β,17α-diol-3,20-dione (1 gm.) in pyridine (5 ml.) add trifluoroacetic anhydride (1 ml.) and stir the reaction mixture at −20°C for 30 minutes. Pour the mixture into dilute hydrochloric acid and filter off and dry the resultant precipitate comprising 9α-fluoro-21-chloro-16α-methyl-1,4-pregnadiene-11β,17α-diol-3,20-dione 11-trifluoroacetate which may be used without further purification in following precedure 8B.

B. 9α-Fluoro-21-Chloro-16α-Methyl-1,4-Pregnadiene-11β,17α-Diol-3,20-Dione 11-Trifluoroacetate 17-Retinoate.

To a solution of 9α-fluoro-21-chloro-16α-methyl-1,4-pregnadiene-11β,17α-diol-3,20-dione 11-trifluoroacetate (522 mg., 1 mmole) in benzene (20 ml.) cool to 0°C under an atmosphere of nitrogen and in the dark add retinoic acid (300 mg., 1 mmole), trifluoroacetic anhydride (0.6 ml.) and p-toluenesulfonic acid (50 mg.). Stir the reaction mixture while allowing it to warm to room temperature. Stir at room temperature for an additional ½ hour, then pour into water and extract with ether. Wash the combined ether extracts several times with aqueous sodium bicarbonate, then with water, dry over magnesium sulfate and evaporate in vacuo to a residue comprising 9α-fluoro-21-chloro-16α-methyl-1,4-pregnadiene-11β,17α-diol-3,20-dione 11-trifluoroacetate 17-retinoate which is purified by chromatography on silica gel GF thick layer plates.

C. 9α-Fluoro-21-Chloro-16α-Methyl-1,4-Pregnadiene-11β,17α-Diol-3,20-Dione 17-Retinoate.

Dissolve the 9α-fluoro-21-chloro-16α-methyl-1,4-pregnadiene-11β,17α-diol-3,20-dione 11-trifluoroacetate 17-retinoate prepared in Example 8B in methanol (25 ml.), then add sodium benzoate (2.5 gms.) and stir for ½ hour at room temperature under an atmosphere of nitrogen. Evaporate the solvent in vacuo and partition the resultant residue between ether and water. Wash the ether layer with water, dry over magnesium sulfate, evaporate in vacuo and chromatograph the resultant residue on silica gel GF thick layer plates eluting with ethly acetate/chloroform (1:2). Remove the steroidal retinoate band from the thick layer plate, extract with ethyl acetate and evaporate in vacuo to a residue comprising 9α-fluoro-21-chloro-16α-methyl-1,4-pregnadiene-11β,17α-diol-3,20-dione 17-retinoate.

EXAMPLE 9

PROCEDURE FOR PREPARING 21-DESOXY-17-RETINOATES FROM 21-HYDROXY 17-RETINOATES

A. 9α-Fluoro-16α-Methyl-1,4-pregnadiene-11β,17α,21-triol-3,20-Dione 17-Retinoate 21-Methanesulfonate.

To a solution of 9α-fluoro-16α-methyl-1,4-pregnadiene-11β,17α,21-triol-3,20-dione 17-retinoate (674 mg., 1 mmole) in pyridine (10 ml.), cool to −20°C under an atmosphere of nitrogen and in the dark add methanesulfonyl chloride (redistilled) (0.6 ml.) and allow the reaction mixture to stand at −20°C overnight. Pour the reaction mixture into dilute hydrochloric acid, filter off the resultant precipitate, wash with water and dry. Purify by crystallization from ether to obtain 9α-fluoro-16α-methyl-1,4-pregnadiene-11β,17α,21-triol-3,20-dione 17-retinoate 21-methanesulfonate.

B. 9α-Fluoro-21-Chloro-16α-Methyl-1,4-Pregnadiene-11β,17α-Diol-3,20-Dione 17-Retinoate.

To a solution of 9α-fluoro-16α-methyl-1,4-pregnadiene-11β,17α,21-triol-3,20-dione 17-retinoate 21-methanesulfonate (75.2 mg., 0.1 mmole) in dimethylformamide (3 ml.) under an atmosphere of nitrogen and in the dark add lithium chloride (43 mg., 1 mmole) and stir the reaction mixture at 50°C for 5 hours. Pour the reaction mixture into water and extract with ether. Wash the combined ether extracts with water, dry over magnesium sulfate and evaporate in vacuo to a residue comprising 9α-fluoro-21-chloro-16α-methyl-1,4-pregnadiene-11β,17α-diol-3,20-dione 17-retinoate.

C. 9α-Fluoro-16α-Methyl-1,4-Pregnadiene-11β,17α-Diol-3,20-Dione 17-Retinoate.

To a solution of 9α-fluoro-16α-methyl-1,4-pregnadiene-11β,17α,21-triol-3,20-dione 17-retinoate 21-methanesulfonate (300 mg.) in dimethylformamide (5 ml.) under an atmosphere of nitrogen and in the dark add acetic acid (5 ml.) containing sodium iodide (300 mg.). Heat the reaction mixture on a water bath for ½ hour, then cool and dilute with ether. Wash the ethereal solution sequentially with water, aqueous sodium bicarbonate and then again with water. Evaporate the ether solution in vacuo and chromatograph the resultant residue on silica gel GF thick layer plates eluting with ethyl acetate/chloroform (1:2). Remove the steroidal retinoate band from the thick layer plate, extract with ethyl acetate and evaporate in vacuo to a residue comprising 9α-fluoro-16α-methyl-1,4-pregnadiene-11β,17α-diol-3,20-dione 17-retinoate.

EXAMPLE 10

9α,11β,21-TRIHALOGENO-16α-METHYL-1,4-PREGNADIENE-17α-OL-3,20-DIONE 17-RETINOATES

A. 9α,21-Dichloro-11β-Fluoro-16α-Methyl-1,4-Pregnadiene-17α-Ol-3,20-Dione 17-Retinoate.

To a solution of 9α,21-dichloro-11β-fluoro-16α-methyl-1,4-pregnadiene-17α-ol-3,20-dione (428 mg., 1 mmole) in benzene (10 ml.) cool to 0°C under an atmosphere of nitrogen and in the dark add retinoic acid (300 mg., 1 mmole), trifluoroacetic anhydride (0.6 ml.) and p-toluenesulfonic acid (50 mg.). Stir the reaction mixture while allowing it to warm to warm temperature for an additional ½ hour. Pour the reaction mixture into water, extract with ether, then wash the combined ether extracts several times with aqueous sodium bicarbonate, then with water. Dry over magnesium sulfate and evaporate in vacuo and chromatograph the resultant product on silica gel GF thick layer plates eluting with ethyl acetate/chloroform (1:2). Remove the steroidal retinoate band from the thick layer plate, extract with ethyl acetate and evaporate in vacuo to a residue comprising 9α,21-dichloro-11β-fluoro-16α- methyl-1,4-pregnadiene-17α-ol-3,20-dione 17-retinoate.

B. 9α,11β-Dichloro-21-Fluoro-16α-Methyl-1,4-Pregnadiene-17α-Ol-3,20-Dione 17-Retinoate.

To a solution of 9α,11β-dichloro-21-fluoro-16α-methyl-1,4-pregnadiene-17α-ol-3,20-dione (856 mg., 2 mmoles) in pyridine (10 ml.) under an atmosphere of nitrogen and in the dark add retinoic acid chloride (1.272 gms., 4 mmoles) and 4-dimethylamino pyridine (50 mg.). Stir the reaction mixture at 50°C under an atmosphere of nitrogen and in the dark overnight then pour into dilute hydrochloric acid and extract with ether. Wash the combined ether extracts with water, dry over magnesium sulfate, evaporate in vacuo and chromatograph the resultant residue over a silica gel column eluting first with petroleum ether, then with petroleum ether/ether solvent mixtures containing increasing amounts of ether and finally eluting with ether. Combine the like steroidal retinoate fractions as determined by thin layer chromatography and evaporate in vacuo to a residue comprising 9α,11β-dichloro-21-fluoro-16α-methyl-1,4-pregnadiene-17α-ol-3,20-dione 17-retinoate.

EXAMPLE 11

PREPARATION OF 9α,11β-DIHALOGENO-21-DESOXY-1,4-PREGNADIENE-17α-OL-3,20-DIONE 17-RETINOATES

Treat each of the following 9α,11β-dihalogeno-21-desoxy-1,4-pregnadiene-17α-ol-3,20-diones in benzene with retinoic acid, trifluoroacetic anhydride and p-toluenesulfonic acid in a manner similar to that described in Example 10A or alternatively, in pyridine with retinoic acid chloride and dimethylamino pyridine in a manner similar to that described in Example 10B.

1. 9α,11β-dichloro-1,4-pregnadiene-17α-ol-3,20-dione,
2. 9α-chloro-11β-fluoro-1,4-pregnadiene-17α-ol-3,20-dione,
3. 9α,11β-dichloro-1,4,6-pregnatriene-17α-ol-3,20-dione,
4. 9α-chloro-11β-fluoro-1,4,6-pregnatriene-17α-ol-3,20-dione,
5. 9α,11β-dichloro-21-fluoro-1,4-pregnadiene-17α-ol-3,20-dione,
6. 9α-chloro-11β,21-difluoro-1,4-pregnadiene-17α-ol-3,20-dione,
7. 9α,11β-dichloro-21-fluoro-1,4,6-pregnatriene-17α-ol-3,20-dione,
8. 9α-chloro-11β,21-difluoro-1,4,6-pregnatriene-17α-ol-3,20-dione,
9. 9α,11β,21-trichloro-1,4-pregnadiene-17α-ol-3,20-dione,
10. 9α,21-dichloro-11β-fluoro-1,4-pregnadiene-17α-ol-3,20-dione,
11. 9α,11β,21-trichloro-1,4,6-pregnatriene-17α-ol-3,20-dione,
12. 9α,21-dichloro-11β-fluoro-1,4,6-pregnatriene-17α-ol-3,20-dione,
13. 9α,11β-dichloro-16α-methyl-1,4-pregnadiene-17α-ol-3,20-dione,
14. 9α-chloro-11β-fluoro-16α-methyl-1,4-pregnadiene-17α-ol-3,20-dione,
15. 9α,11β-dichloro-16α-methyl-1,4,6-pregnatriene-17α-ol-3,20-dione,
16. 9α-chloro-11β-fluoro-16α-methyl-1,4,6-pregnatriene-17α-ol-3,20-dione,
17. 9α,11β-dichloro-21-fluoro-16α-methyl-1,4-pregnadiene-17α-ol-3,20-dione,
18. 9α-chloro-11α,21-difluoro-16α-methyl-1,4-pregnadiene-17α-ol-3,20-dione,
19. 9α,11β-dichloro-21-fluoro-16α-methyl-1,4,6-pregnatriene-17α-ol-3,20-dione,
20. 9α-chloro-11β,21-difluoro-16α-methyl-1,4,6-pregnatriene-17α-ol-3,20-dione,
21. 9α,11β,21-trichloro-16α-methyl-1,4-pregnadiene-17α-ol-3,20-dione,
22. 9α,21-dichloro-11β-fluoro-16α-methyl-1,4-pregnadiene-17α-ol-3,20-dione,
23. 9α,11β,21-trichloro-16α-methyl-1,4,6-pregnatriene-17α-ol-3,20-dione,
24. 9α,21-dichloro-11β-fluoro-16α-methyl-1,4,6-pregnatriene-17α-ol-3,20-dione,
25. 9α,11β-dichloro-16β-methyl-1,4-pregnadiene-17α-ol-3,20-dione,
26. 9α-chloro-11β-fluoro-16β-methyl-1,4-pregnadiene-17α-ol-3,20-dione,
27. 9α,11β-dichloro-16β-methyl-1,4,6-pregnatriene-17α-ol-3,20-dione,
28. 9α-chloro-11β-fluoro-16β-methyl-1,4,6-pregnatriene-17α-ol-3,20-dione,
29. 9α,11β-dichloro-21-fluoro-16β-methyl-1,4-pregnadiene-17α-ol-3,20-dione,
30. 9α-chloro-11β,21-difluoro-16β-methyl-1,4-pregnadiene-17α-ol-3,20-dione,
31. 9α,11β-dichloro-21-fluoro-16β-methyl-1,4,6-pregnatriene-17α-ol-3,20-dione,
32. 9α-chloro-11β,21-difluoro-16β-methyl-1,4,6-pregnatriene-17α-ol-3,20-dione,
33. 9α,11β,21-trichloro-16β-methyl-1,4-pregnadiene-17α-ol-3,20-dione,
34. 9α,21-dichloro-11β-fluoro-16β-methyl-1,4-pregnadiene-17α-ol-3,20-dione,
35. 9α,11β,21-trichloro-16β-methyl-1,4,6-pregnatriene-17α-ol-3,20-dione,
36. 9α,21-dichloro-11β-fluoro-16β-methyl-1,4,6-pregnatriene-17α-ol-3,20-dione,
37. 6α-fluoro-9α,11β-dichloro-1,4-pregnadiene-17α-ol-3,20-dione,
38. 6-fluoro-9α,11β-dichloro-1,4,6-pregnatriene-17α-ol-3,20-dione,
39. 6α,9α,11β-trichloro-16α-methyl-1,4-pregnadiene-17α-ol-3,20-dione,
40. 6-fluoro-9α,11β-dichloro-16α-methyl-1,4,6-pregnatriene-17α-ol-3,20-dione,
41. 6α-fluoro-9α,11β-dichloro-16β-methyl-1,4-pregnadiene-17α-ol-3,20-dione,
42. 6-fluoro-9α,11β-dichloro-16β-methyl-1,4,6-pregnatriene-17α-ol-3,20-dione,
43. 6α-fluoro-9α,11β,21-trichloro-1,4-pregnadiene-17α-ol-3,20-dione,
44. 6-fluoro-9α,11β,21-trichloro-1,4,6-pregnatriene-17α-ol-3,20-dione,
45. 6α,9α,11β,21-tetrachloro-16α-methyl-1,4-pregnadiene-17α-ol-3,20-dione,
46. 6-fluoro-9α,11β,21-trichloro-16α-methyl-1,4,6-pregnatriene-17α-ol-3,20-dione,
47. 6α-fluoro-9α,11β,21-trichloro-16β-methyl-1,4-pregnadiene-17α-ol-3,20-dione,
48. 6-fluoro-9α,11β,21-trichloro-16β-methyl-1,4,6-pregnatriene-17β-ol-3,20-dione,
49. 6α,21-difluoro-9α,11β-dichloro-1,4-pregnadiene-17α-ol-3,20-dione,
50. 6,21-difluoro-9α,11β-dichloro-1,4,6-pregnatriene-17α-ol-3,20-dione, 51. 6α,9α,11β-trichloro-21-fluoro-16α-methyl-1,4-pregnadiene-17α-ol-3,20-dione,
52. 6,21-difluoro-9α,11β-dichloro-16α-methyl-1,4,6-pregnatriene-17α-ol-3,20-dione,
53. 6α,21-difluoro-9α,11β-dichloro-16β-methyl-1,4-pregnadiene-17α-ol-3,20-dione,
54. 6,21-difluoro-9α,11β-dichloro-16β-methyl-1,4,6-pregnatriene-17α-ol-3,20-dione,
55. 6,9α,11β-trichloro-21-fluoro-16β-methyl-1,4,6-pregnatriene-17α-ol-3,20-dione,
56. 6,9α,11β-trichloro-21-fluoro-16α-methyl-1,4,6-pregnatriene-17α-ol-3,20-dione.

Isolate and purify each of the resultant respective products in a manner similar to that described in Example 10A or 10B, and there will be obtained the corresponding 17-retinoic acid ester of each of the starting compounds listed hereinabove, respectively.

EXAMPLE 12

PREPARATION OF OTHER 21-DESOXY-4-PREGNENE-11β,17α-DIOL-3,20-DIONE 17-RETINOATES AND 1-DEHYDRO, 6-DEHYDRO AND 1,6-BISDEHYDRO ANALOGS THEREOF

A. 21-Desoxy-4-Pregnene-11β,17α-Diol-3,20-Dione 11-Trifluoroacetates.

In a manner similar to that described in Example 8A treat each of the following 21-desoxy-4-pregnene-11β,17α-diol-3,20-diones in pyridine with trifluoroacetic anhydride:

1. 9α-fluoro-1,4-pregnadiene-11β,17α-diol-3,20-dione,
2. 1,4-pregnadiene-11β,17α-diol-3,20-dione,
3. 9α,21-difluoro-1,4-pregnadiene-11β,17α-diol-3,20-dione,
4. 21-fluoro-1,4-pregnadiene-11β,17α-diol-3,20-dione,
5. 9α-fluoro-21-chloro-1,4-pregnadiene-11β,17α-diol-3,20-dione,
6. 21-chloro-1,4-pregnadiene-11β,17α-diol-3,20-dione,
7. 16α-methyl-1,4-pregnadiene-11β,17α-diol-3,20-dione,
8. 9α-fluoro-16α-methyl-1,4-pregnadiene-11β,17α-diol-3,20-dione,
9. 16β-methyl-1,4-pregnadiene-11β,17α-diol-3,20-dione,
10. 9α-fluoro-16β-methyl-1,4-pregnadiene-11β,17α-diol-3,20-dione,
11. 16-methylene-1,4-pregnadiene-11β,17α-diol-3,20-dione,
12. 9α-fluoro-16-methylene-1,4-pregnadiene-11β,17α-diol-3,20-dione,
13. 16α-methyl-21-fluoro-1,4-pregnadiene-11β,17α-diol-3,20-dione,
14. 16α-methyl-21-chloro-1,4-pregnadiene-11β,17α-diol-3,20-dione,
15. 9α,21-difluoro-16α-methyl-1,4-pregnadiene-11β,17α-diol-3,20-dione,
16. 16β-methyl-21-fluoro-1,4-pregnadiene-11β,17α-diol-3,20-dione,
17. 16β-methyl-21-chloro-1,4-pregnadiene-11β,17α-diol-3,20-dione,
18. 9α,21-difluoro-16β-methyl-1,4-pregnadiene-11β,17α-diol-3,20-dione,
19. 16-methylene-21-fluoro-1,4-pregnadiene-11β,17α-diol-3,20-dione,
20. 16-methylene-21-chloro-1,4-pregnadiene-11β,17α-diol-3,20-dione,
21. 9α,21-difluoro-16-methylene-1,4-pregnadiene-11β,17α-diol-3,20-dione,
22. 6α-fluoro-16α-methyl-1,4-pregnadiene-11β,17α-diol-3,20-dione,
23. 6α,9α-difluoro-16α-methyl-1,4-pregnadiene-11β,17α-diol-3,20-dione,
24. 6α,21-difluoro-16α-methyl-1,4-pregnadiene-11β,17α-diol-3,20-dione,
25. 6α-fluoro-16β-methyl-1,4-pregnadiene-11β,17α-diol-3,20-dione,
26. 6α,9α-difluoro-16β-methyl-1,4-pregnadiene-11β,17α-diol-3,20-dione,
27. 6α,21-difluoro-16β-methyl-1,4-pregnadiene-11β,17α-diol-3,20-dione,
28. 6α-fluoro-16-methylene-1,4-pregnadiene-11β,17α-diol-3,20-dione,
29. 6α,9α-difluoro-16-methylene-1,4-pregnadiene-11α,17α-diol-3,20-dione,
30. 6α,21-difluoro-16-methylene-1,4-pregnadiene-11β,17α-diol-3,20-dione,
31. 6-fluoro-16α-methyl-1,4,6-pregnatriene-11β,17α-diol-3,20-dione,
32. 6,9α-difluoro-16α-methyl-1,4,6-pregnatriene-11β,17α-diol-3,20-dione,
33. 6,21-difluoro-16α-methyl-1,4,6-pregnatriene-11β,17α-diol-3,20-dione,
34. 6-fluoro-16β-methyl-1,4,6-pregnatriene-11β,17α-diol-3,20-dione,
35. 6,9α-difluoro-16β-methyl-1,4,6-pregnatriene-11β,17α-diol-3,20-dione,
36. 6,21-difluoro-16β-methyl-1,4,6-pregnatriene-11β,17α-diol-3,20-dione,
37. 6-fluoro-16-methylene-1,4,6-pregnatriene-11β,17α-diol-3,20-dione,
38. 6,9α-difluoro-16-methylene-1,4,6-pregnatriene-11β,17α-diol-3,20-dione,
39. 6,21-difluoro-16-methylene-1,4,6-pregnatriene-11β,17α-diol-3,20-dione,
40. 2'-phenyl-11β,17α-dihydroxy-16α-methyl-20-keto-4,6-pregnadieno-[3,2-c]-pyrazole,
41. 2'-phenyl-9α-fluoro-11β,17α-dihydroxy-16α-methyl-20-keto-4,6-pregnadieno-[3,2-c]-pyrazole,
42. 2'-phenyl-9α-fluoro-21-chloro-11β,17α-dihydroxy-16α-methyl-4,6-pregnadieno-[3,2-c]-pyrazole,
43. 2'-phenyl-11β,17α-dihydroxy-16β-methyl-20-keto-4,6-pregnadieno-[3,2-c]-pyrazole,
44. 2'-phenyl-9α-fluoro-11β,17α-dihydroxy-16β-methyl-20-keto-4,6-pregnadieno-[3,2-c]-pyrazole,
45. 2'-phenyl-9α-fluoro-21-chloro-11β,17α-dihydroxy-16β-methyl-20-keto-4,6-pregnadieno-[3,2-c]-pyrazole,
46. 2'-phenyl-11β,17α-dihydroxy-16-methylene-20-keto-4,6-pregnadieno-[3,2-c]-pyrazole,
47. 2'-phenyl-9α-fluoro-11β,17α-dihydroxy-16-methylene-20-keto-4,6-pregnadieno-[3,2-c]-pyrazole,
48. 2'-phenyl-9α-fluoro-21-chloro-11β,17α-dihydroxy-16-methylene-20-keto-4,6-pregnadieno-[3,2-c]-pyrazole,
49. 2'phenyl-6,16α-dimethyl-9α-fluoro-11β,17α-dihydroxy-20-keto-4,6-pregnadieno-[3,2-c]pyrazole.

Isolate and purify each of the resultant products in a manner similar to that described in Example 8A to obtain the 11-trifluoroacetate ester, respectively, of each of the above listed 11β-hydroxy starting compounds.

B. 21-Desoxy-4-Pregnene-11β,17α-Diol-3,20-Dione 11-Trifluoroacetate 17-Retinoates.

In a manner similar to that described in Example 8B treat each of the 49 11-trifluoroacetate ester derivatives prepared in Example 12A in benzene at 0°C under an atmosphere of nitrogen and in the dark with retinoic acid, trifluoroacetic anhydride and p-toluenesulfonic acid. Isolate and purify each of the resultant products in a manner similar to that described in Example 8B to obtain the corresponding 11-trifluoroacetate 17-retinoate ester derivatives of each of the 49 11β,17α-dihydroxy starting compounds listed in Example 12A.

C. 21-Desoxy-4-Pregnene-11β,17α-Diol-3,20-Dione 17-Retinoates.

In a manner similar to that described in Example 8C, treat each of the 11β-trifluoroacetate 17α-retinoate ester derivatives prepared in above Example 12B in methanol with sodium benzoate at room temperature under an atmosphere of nitrogen. Isolate and purify each of the resultant respective products in a manner similar to that described in Example 8C to obtain the 17-retinoate esters of each of the 49 4-pregnene-11β,17α-diol-3,20-dione starting compounds listed in above Example 12A.

EXAMPLE 13

PREPARATION OF 21-RETINOATES, 17α-RETINOATES, AND 17α, 21-DIRETINOATES OF 4-PREGNENE-3,20-DIONES AND 1-DEHYDRO, 6-DEHYDRO, AND 1,6-BISDEHYDRO ANALOGS THEREOF

A. 4-Pregnene-21-Ol-3,20-Dione 21-Retinoates and 1-Dehydro, 6-Dehydro and 1,6-Bisdehydro Analogs Thereof.

In a manner similar to that described in Example 1-A treat each of the following 4-pregnene-21-ol-3,20-diones in dry tetrahydrofuran under an atmosphere of nitrogen in the dark with N-retinoylimidazole and sodium methoxide and then isolating and purifying the resultant products thereby obtained to obtain the corresponding 21-retinoate esters of the following listed 21-hydroxy starting steroids.

1. 9α-fluoro-1,4-pregnadiene-11β,17α,21-triol-3,20-dione,
2. 9α-chloro-1,4-pregnadiene-11β,17α,21-triol-3,20-dione,
3. 9α-fluoro-4-pregnene-11β,17α,21-triol-3,20-dione,
4. 9α-chloro-4-pregnene-11β,17α,21-triol-3,20-dione,
5. 16α-methyl-1,4-pregnadiene-11β,17α,21-triol-3,20-dione,
6. 9α-chloro-16α-methyl-1,4-pregnadiene-11β,17α,21-triol-3,20-dione,
7. 16α-methyl-1,4-pregnadiene-11β,17α,21-triol-3,20-dione,
8. 9α-chloro-16β-methyl-1,4-pregnadiene-11β,17α,21-triol-3,20-dione,
9. 16-methylene-1,4-pregnadiene-11β,17α,21-triol-3,20-dione,
10. 16-methylene-9α-chloro-1,4-pregnadiene-11β,17α,21-triol-3,20-dione,
11. 9α-fluoro-16-methylene-1,4-pregnadiene-11β,17α,21-triol-3,20-dione,
12. 16α-methyl-4-pregnene-11β,17α,21-3,20-dione,
13. 9α-fluoro-16α-methyl-4-pregnene-11β,17α,21-triol-3,20-dione,
14. 9α-chloro-16α-methyl-4-pregnene-11β,17α,21-triol-3,20-dione,
15. 16β-methyl-4-pregnene-11β,17α,21-triol-3,20-dione,
16. 9α-fluoro-16β-methyl-4-pregnene-11β,17α,21-triol-3,20-dione,
17. 9α-chloro-16β-methyl-4-pregnene-11β,17α,21-triol-3,20-dione,
18. 16-methylene-4-pregnene-11β,17α,21-triol-3,20-dione,
19. 9α-fluoro-16-methylene-4-pregnene-11β,17α,21-triol-3,20-dione,
20. 9α-chloro-16-methylene-4-pregnene-11β,17α,21-triol-3,20-dione,
21. 6α-fluoro-1,4-pregnadiene-11β,17α,21-triol-3,20-dione,
22. 6α,9α-difluoro-1,4-pregnadiene-11β,17α,21-triol-3,20-dione,
23. 6α-fluoro-9α-chloro-1,4-pregnadiene-11β,17α,21-triol-3,20-dione,
24. 2-chloro-6α-fluoro-1,4-pregnadiene-11β,17α,21-triol-3,20-dione,
25. 2-chloro-6α,9α-difluoro-1,4-pregnadiene-11β,17α,21-triol-3,20-dione,
26. 2,9α-dichloro-6α-fluoro-1,4-pregnadiene-11β,17α,21-triol-3,20-dione,
27. 6α-4-pregnene-11β,17α,21-triol-3,20-dione,
28. 6α,9α-difluoro-4-pregnene-11β,17α,21-triol-3,20-dione,
29. 6α-fluoro-9α-chloro-4-pregnadiene-11β,17α,21-triol-3,20-dione,
30. 6α,9α-difluoro-16α-methyl-1,4-pregnadiene-11β,17α,21-triol-3,20-dione,
31. 6α,9α-difluoro-16α-methyl-1,4-pregnadiene-11β,17α,21-triol-3,20-dione,
32. 6α,9α-dichloro-16α-methyl-1,4-pregnadiene-11β,17α,21-triol-3,20dione,
33. 6α-fluoro-16β-methyl-1,4-pregnadiene-11β,17α,21-triol-3,20-dione,
34. 6α,9α-difluoro-16β-methyl-1,4-pregnadiene-11β,17α,21-triol-3,20-dione,
35. 6α-fluoro-9α-chloro-16β-methyl-1,4-pregnadiene-11β,17α,21-triol-3,20-dione,
36. 6α-fluoro-16-methylene-1,4-pregnadiene-11β,17α,21-triol-3,20-dione,
37. 6α,9α-difluoro-16-methylene-1,4-pregnadiene-11β,17α,21-triol-3,20-dione,
38. 6α-fluoro-9α-chloro-16-methylene-1,4-pregnadiene-11β,17α,21-triol-3,20-dione,
39. 16α-methyl-4,6-pregnadiene-11β,17α,21-triol-3,20-dione,
40. 9α-fluoro-16α-methyl-4,6-pregnadiene-11β,17α,21-triol-3,20-dione,
41. 9α-chloro-16α-methyl-4,6-pregnadiene-11β,17α,21-triol-3,20-dione,
42. 16β-methyl-4,6-pregnadiene-11β,17α,21-3,20-dione,
43. 9α-fluoro-16β-methyl-4,6-pregnadiene-11β,17α,21-3,20-dione,
44. 9α-chloro-16β-methyl-4,6-pregnadiene-11β,17α,21-triol-3,20-dione,
45. 16-methylene-4,6-pregnadiene-11β,17α,21-triol-3,20-dione,
46. 9α-fluoro-16-methylene-4,6-pregnadiene-11β,17α,21-triol-3,20-dione, 47. 9α-chloro-16-methylene-4,6-pregnadiene-11β,17α,21-triol-3,20-dione,
48. 6-fluoro-1,4,6-pregnatriene-11β,17α,21-triol-3,20-dione,
49. 6,9α-difluoro-1,4,6-pregnatriene-11β,17α,21-triol-3,20-dione,
50. 6-fluoro-9α-chloro-1,4,6-pregnatriene-11β,17α,21-triol-3,20-dione,
51. 6-chloro-1,4,6-pregnatriene-11β,17α,21-triol-3,20-dione,
52. 6-chloro-9α-fluoro-1,4,6-pregnatriene-11β,17α,21-triol-3,20-dione,
53. 6,9α-dichloro-1,4,6-pregnatriene-11β,17α,21-triol-3,20-dione,
54. 6-methyl-1,4,6-pregnatriene-11β,17α,21-triol-3,20-dione,
55. 6-methyl-9α-fluoro-1,4,6-pregnatriene-11β,17α,21-triol-3,20-dione,
56. 6-methyl-9α-chloro-1,4,6-pregnatriene-11β,17α,21-triol-3,20-dione,
57. 6-azido-1,4,6-pregnatriene-11β,17α,21-triol-3,20-dione,
58. 6-azido-9α-fluoro-1,4,6-pregnatriene-11β,17α,21-triol-3,20-dione,
59. 6-azido-9α-chloro-1,4,6-pregnatriene-11β,17α,21-triol-3,20-dione,
60. 6-fluoro-4,6-pregnadiene-11β,17α,21-triol-3,20-dione,
61. 6,9α-difluoro-4,6-pregnadiene-11β,17α,21-triol-3,20-dione,
62. 6-fluoro-9α-chloro-4,6-pregnadiene-11β,17α,21-triol-3,20-dione,
63. 6-chloro-4,6-pregnadiene-11β,17α,21-triol-3,20-dione,
64. 6-chloro-9α-fluoro-4,6-pregnadiene-11β,17α,21-triol-3,20-dione,
65. 6,9α-dichloro-4,6-pregnadiene-11β,17α,21-triol-3,20-dione,
66. 6-methyl-4,6-pregnadiene-11β,17α,21-triol-3,20-dione,
67. 6-methyl-9α-fluoro-4,6-pregnadiene-11β,17α,21-triol-3,20-dione,
68. 6-methyl-9α-chloro-4,6-pregnadiene-11β,17α,21-triol-3,20-dione,
69. 6-azido-4,6-pregnadiene-11β,17α,21-triol-3,20-dione,
70. 6-azido-9α-fluoro-4,6-pregnadiene-11β,17α,21-triol-3,20-dione,
71. 6-azido-9α-chloro-4,6-pregnadiene-11β,17α,21-triol-3,20-dione,
72. 6-fluoro-16α-methyl-1,4,6-pregnatriene-11β,17α,21-triol-3,20-dione,
73. 6,9α-difluoro-16α-methyl-1,4,6-pregnatriene-11β,17α,21-triol-3,20-dione,
74. 6-fluoro-9α-chloro-16α-methyl-1,4,6-pregnatriene-11β,17α,21-triol-3,20-dione,
75. 6-fluoro-16β-methyl-1,4,6-pregnatriene-11β,17α,21-triol-3,20-dione,
76. 6,9α-difluoro-16β-methyl-1,4,6-pregnatriene-11β,17α,21-triol-3,20-dione,
77. 6-fluoro-9α-chloro-16β-methyl-1,4,6-pregnatriene-11β,17α,21-triol-3,20-dione,
78. 6-fluoro-16-methylene-1,4,6-pregnatriene-11β,17α,21-triol-3,20-dione,
79. 6,9α-dichloro-16-methylene-1,4,6-pregnatriene-11β,17α,21-triol-3,20-dione,
80. 6-fluoro-9α-chloro-16-methylene-1,4,6-pregnatriene-11β,17α,21-triol-3,20-dione,
81. 6-azido-16α-methyl-1,4,6-pregnatriene-11β,17α,21-triol-3,20-dione,
82. 6-azido-9α-fluoro-16α-methyl-1,4,6-pregnatriene-11β,17α,21-triol-3,20-dione,
83. 6-azido-9α-chloro-16α-methyl-1,4,6-pregnatriene-11β,17α,21-triol-3,20-dione,
84. 6-azido-16β-methyl-1,4,6-pregnatriene-11β,17α,21-triol-3,20-dione,
85. 6-azido-9α-fluoro-16β-methyl-1,4,6-pregnatriene-11β,17α,21-triol-3,20-dione,
86. 6-azido-9α-chloro-16β-methyl-1,4,6-pregnatriene-11β,17α,21-triol-3,20dione,
87. 6-azido-16-methylene-1,4,6-pregnatriene-11β,17α,21-triol-3,20-dione,
88. 6-azido-9α-fluoro-16-methylene-1,4,6-pregnatriene-11β,17α, 21-triol-3,20-dione,
89. 6-azido-9α-chloro-16-methylene-1,4,6-pregnatriene-11β,17α,21-triol-3,20-dione,
90. 6-fluoro-16α-methyl-4,6-pregnadiene-11β,17α,21-triol-3,20-dione,
91. 6,9α-difluoro-16α-methyl-4,6-pregnadiene-11β,17α,21-triol-3,20-dione,
92. 6-fluoro-9α-chloro-16α-methyl-4,6-pregnadiene-11β,17α,21-triol-3,20-dione,
93. 6-fluoro-16β-methyl-4,6-pregnadiene-11β,17α,21-triol-3,20-dione,
94. 6,9α-difluoro-16β-methyl-4,6-pregnadiene-11β,17α,21-triol-3,20-dione,
95. 6-fluoro-9α-chloro-16β-methyl-4,6-pregnadiene-11β,17α,21-triol-3,20-dione,
96. 6-fluoro-16-methylene-4,6-pregnadiene-11β,17α,21-triol-3,20-dione,
97. 6,9α-difluoro-16-methylenee-4,6-pregnadiene-11β,17α,21-triol-3,20-dione,
98. 6-fluoro-9α-chloro-16-methylene-4,6-pregnadiene-11β,17α,21-triol-3,20-dione,
99. 6-azido-16α-methyl-4,6pregnadiene-11β,17α,21-triol-3,20-dione,
100. 6-azido-9α-fluoro-16α-methyl-4,6-pregnadiene-11β,17α,21-triol-3,20dione,
101. 6-azido-9α-methyl-4,6-pregnadiene-11β,17α,21-triol-3,20-dione,
102. 6-azido-16β-methyl-4,6-pregnadiene-11β, 17α, 21-triol-3,20-dione,
103. 6-azido-9α-fluoro-16β-methyl-4,6-pregnadiene-11β,17α, 21-triol-3,20-dione,
104. 6-azido-9α-chloro-16β-methyl-4,6-pregnadiene-11β,17α,21-triol-3,20-dione,
105. 6-azido-16-methylene-4,6-pregnadiene-11β,17α,21-triol-3,20-dione,
106. 6-azido-9α-fluoro-16-methylene-4,6-pregnadiene-11β,17α,21-triol-3,20-dione,
107. 6-azido-9α-chloro-16-methylene-4,6-pregnadiene-11β,17α,21-triol-3,20-dione,
108. 9α-fluoro-1,4-pregnadiene-17α,21-diol-3,11,20-trione,
109. 9α-fluoro-4-pregnene-17α,21-diol-3,11,20trione,
110. 16α-methyl-1,4-pregnadiene-17α,21-diol-3,11,20-trione,
111. 16β-methyl-1,4-pregnadiene-17α,21-diol-3,11,20-trione,
112. 16-methylene-1,4-pregnadiene-17α,21-diol-3,11,20-trione,
113. 16α-methyl-4-pregnene-17α,21-diol-3,11,20-trione,
114. 9α-fluoro-16α-methyl-4-pregnene-17α,21-diol-3,11,20-trione, 115. 16β-methyl-4-pregnene-17α,21-diol-3,11,20-trione,
116. 9α-fluoro-16β-methyl-4-pregnene-17α,21-diol-3,11,20-trione,
117. 16-methylene-4-pregnene-17α,21-diol-3,11,20-trione,
118. 9α-fluoro-16-methylene-4-pregnene-17α,21-diol-3,11,20-trione,
119. 6α-fluoro-1,4-pregnadiene-17α,21-diol-3,11,20,-trione,
120. 6α,9α-difluoro-1,4-pregnadiene-17α,21-diol-3,11,20-trione,
121. 6α-fluoro-4-pregnene-17α,21-diol-3,11,20-trione,
122. 6α,9α-difluoro-4-pregnene-17α,21-diol-3,11,20-trione,
123. 6α-fluoro-16α-methyl-1,4-pregnadiene-11β,17αdiol-3,11,20-trione,
124. 6α,9α-difluoro-16α-methyl-1,4-pregnadiene-17α,21-diol-3,11,20-trione,
125. 6α-fluoro-16β-methyl-1,4-pregnadiene-17α,21-diol-3,11,20-trione,
126. 6α,9α-difluoro-16β-methyl-1,4-pregnadiene-17α,21-diol-3,11,20-trione,
127. 6α-fluoro-16-methylene-1,4-pregnadiene-17α,21-diol-3,11,20-trione,
128. 6α,9α-difluoro-16-methylene-1,4-pregnadiene-17α,21-diol-3,11,20-trione,
129. 1,4,6-pregnatriene-17α,21-diol-3,11,20,-trione,
130. 9α-fluoro-1,4,6-pregnatriene-17α,21-diol-3,11,20,-trione,
131. 4,6-pregnadiene-17α,21-diol-3,11,20-trione,
132. 9α-fluoro-4,6-pregnadiene-17α,21-diol-3,11,20-trione,
133. 16α-methyl-1,4,6-pregnatriene-17α,21-diol-3,11,20-trione,
134. 9α-fluoro-16α-methyl-1,4,6-pregnatriene-17α,21-diol-3,11,20-trione,
135. 16β-methyl-1,4,6-pregnatriene-17α,21-diol-3,11,20-trione,
136. 9α-fluoro-16β-methyl-1,4,6-pregnatriene-17α,21-diol-3,11,20-trione,
137. 16-methylene-1,4,6-pregnatriene-17α,21-diol-3,11,20-trione,
138. 9α-fluoro-16-methylene-1,4,6-pregnatriene-17α,21-diol-3,11,20-trione,
139. 6-fluoro-1,4,6-pregnatriene-17α,21-diol-3,11,20-trione,
140. 6,9α-difluoro-1,4,6-pregnatriene-17α,21-diol-3,11,20-trione,
141. 6-chloro-1,4,6-pregnatriene-17α,21-diol-3,11,10-trione,
142. 6-chloro-9α-fluoro-1,4,6-pregnatriene-17α,21-diol-3,11,20-trione,
143. 6-methyl-1,4,6-pregnatriene-17α,21-diol-3,11,20-trione,
144. 6-methyl-9α-fluoro-1,4,6-pregnatriene-17α,21-diol-3,11,20-trione,
145. 6-azido-1,4,6-pregnatriene-17α,21-diol-3,11,20-trione,
146. 6-azido-9α-fluoro-1,4,6-pregnatriene-17α,21-diol-3,11,20-trione,
147. 6-fluoro-16α-methyl-1,4,6-pregnatriene-17α,21-diol-3,11,20-trione,
148. 6,9α-difluoro-16α-methyl-1,4,6-pregnatriene-17α,21-diol-3,11,20-trione,
149. 6-fluoro-16β-methyl-1,4,6-pregnatriene-17α,21-diol-3,11,20-trione,
150. 6,9α-difluoro-16β-methyl-1,4,6-pregnatriene-11β,17α-diol-3,11,20-trione,
151. 6-fluoro-16-methylene-1,4,6-pregnatriene-17α,21-diol-3,11,20-trione,
152. 6,9α-difluoro-16-methylene-1,4,6-pregnatriene-17α,21-diol-3,11,20-trione,
153. 6-azido-6α-methyl-1,4,6-pregnatriene-17α,21-diol-3,11,20-trione,
154. 6-azido-9α-fluoro-16α-methyl-1,4,6-pregnatriene-17α,21-diol-3,11,20-trione,
155. 6-azido-16β-methyl-1,4,6-pregnatriene-17α,21-diol-3,11,20-trione,
156. 6-azido-9α-fluoro-16αmethyl-1,4,6-pregnatriene-17α,21-diol-3,11,20-trione,
157. 6-azido-16-methylene-1,4,6-pregnatriene-17α,21-diol-3,11,20-trione,
158. 6-azido-9α-fluoro-16-methylene-1,4,6-pregnatriene-17α,21-diol-3,11,20-trione,
159. 9α,11β-dichloro-1,4-pregnadiene-17α,21-diol-3,20-dione,
160. 9α-chloro-11β-fluoro-1,4-pregnadiene-17α,21-diol-3,20-dione,
161. 9α,11β-dichloro-1,4,6-pregnatriene-17α,21-diol-3,20-dione,
162. 9α-chloro-11β-fluoro-1,4,6-pregnatriene-17α,21-diol-3,20-dione,
163. 9α,11β-dichloro-4-pregnene-17α,21-diol-3,20-dione,
164. 9α-chloro-11β-fluoro-4-pregnene-17α,21-diol-3,20-dione
165. 9α,11β-dichloro-4,6-pregnadiene-17α,21-diol-3,20-dione,
166. 9α-chloro-11β-fluoro-4,6-pregnadiene-17α,21-diol-3,20,-dione,
167. 9α,11β-dichloro-16α-methyl-1,4-pregnadiene-17α,21-diol-3,20-dione,
168. 9α-chloro-11β-fluoro-16α-methyl-1,4-pregnadiene-17α,21-diol-3,20-dione,
169. 9α,11β-dichloro-16α-methyl-1,4,6-pregnatriene 17α,21-diol-3,20-dione,
170. 9α-chloro-11β-fluoro-16α-methyl-1,4,6-pregnatriene-17α,21-diol-3,20-dione,
171. 9α, 11β-dichloro-16β-methyl-1,4-pregnadiene-17α,21-diol-3,20-dione,
172. 9α-chloro-11β-fluoro-16β-methyl-1,4-pregnadiene-17α,21-diol-3,20-dione,
173. 9α,11β,-dichloro-16β-methyl-1,4,6-pregnatriene-17α,21-diol-3,20-dione,
174. 9α-chloro-11β-fluoro-16β-methyl-1,4,6-pregnatriene-17α,21-diol-3,20-dione,
175. 9α,11β-dichloro-16-methylene-1,4-pregnadiene-17α,21-diol-3,20-dione,
176. 9α-chloro-11β-fluoro-16-methylene-1,4-pregnadiene-17α,21-diol-3,20-dione,
177. 9α,11β-dichloro-16-methylene-1,4,6-pregnatriene-17α,21-diol-3,20-dione,
178. 9α-chloro-11β-fluoro-16-methylene-1,4,6-pregnatriene-17α,21-diol-3,20-dione,
179. 6α-fluoro-9α,11β-dichloro-1,4-pregnadiene-17α,21-diol-3,20-dione,
180. 6α-fluoro-9α,11β-dichloro-4-pregnene-17α,21-diol-3,20-dione,
181. 6α-fluoro-9α, 11β-dichloro-16α-methyl-1,4-pregnadiene-17α,21-diol-3,20-dione,
182. 9α,11β-dichloro-6α-fluoro-16β-methyl-1,4-pregnadiene-17β,21-diol-3,20-dione,
183. 9α,11β-dichloro-6α-fluoro-16-methylene-1,4-pregnadiene-17α,21-diol-3,20-dione, 184. 6α-fluoro-9α,11β-dichloro-16α-methyl-4-pregnene-17α,21-diol-3,20-dione,
185. 6α-fluoro-9α,11β-dichloro-16β-methyl-4-pregnene-17α,21-diol-3,20-dione,
186. 6α-fluoro-9α,11β-dichloro-16-methylene-4-pregnene-17α,21-diol-3,20-dione,
187. 1,4-pregnadiene-11β,21-diol-3,20-dione,
188. 9α-fluoro-1,4-pregnadiene-11β,21-diol-3,20-dione,
189. 4-pregnene-11β,21-diol-3,20-dione,
190. 9α-fluoro-4-pregnene-11β,21-diol-3,20-dione,
191. 16α-methyl-1,4-pregnadiene-11β,21-diol-3,20-dione,
192. 9α-fluoro-16α-methyl-1,4-pregnadiene-11β,21-diol-3,20-dione,
193. 16β-methyl-1,4-pregnadiene-11β,21-diol-3,20-dione,
194. 9α-fluoro-16β-methyl-1,4-pregnadiene-11β,21-diol-3,20-dione,
195. 16-methylene-1,4-pregnadiene-11β,21-diol-3,20-dione,
196. 9α-fluoro-16-methylene-1,4-pregnadiene-11β,21-diol-3,20-dione,
197. 16α-methyl-4-pregnene-11β,21-diol-3,20-dione,
198. 9α-fluoro-16α-methyl-4-pregnene-11β,21-diol-3,20-dione,
199. 16β-methyl-4-pregnene-11β,21-diol-3,20-dione,
200. 9α-fluoro-16β-methyl-4-pregnene-11β,21-diol-3,20-dione,
201. 16-methylene-4-pregnene-11β,21-diol-3,20-dione,
202. 9α-fluoro-16-methylene-4-pregnene-11β,21-diol-3,20-dione,
203. 6α-fluoro-16α-methyl-1,4-pregnadiene-11α,21-diol-3,20-dione,
204. 6α,9α-difluoro-16α-methyl-1,4-pregnadiene-11β,21-diol-3,20-dione,
205. 6α-fluoro-16β-methyl-1,4-pregnadiene-11β,21-diol-3,20-dione,
206. 6α,9α-difluoro-16β-methyl-1,4-pregnadiene-11β,21-diol-3,20-dione,
207. 6α-fluoro-16-methylene-1,4-pregnadiene-11β,21-diol-3,20-dione,
208. 6α,9α-difluoro-16-methylene-1,4-pregnadiene-11β,21-diol-3,20-dione,
209. 6α-fluoro-16α-methyl-1,4-pregnadiene-11β,21-diol-3,20-dione,
210. 6α,9α-difluoro-16β-methyl-1,4-pregnadiene-11α,21-diol-3,20-dione,
211. 1,4-pregnadiene-11β,16α,17α,21-tetrol-3,20-dione,
212. 9α-fluoro-1,4-pregnadiene-11β,16α,17α,21-tetrol-3,20-dione,
213. 4-pregnene-11β,16α,17α,21-tetrol-3,20-dione,
214. 9α-fluoro-4-pregnene-11β,16α,17α,21-tetrol-3,20-dione,
215. 1.4-pregnadiene-11β,16α,17α,21-tetrol-3,20-dione, 16-acetate,
216. 9α-fluoro-1,4-pregnadiene-11β,16α,17α,21-tetrol-3,20-dione 16-acetate,
217. 16α,17α-isopropylidenedioxy-1,4-pregnadiene-11β,21-diol-3,20-dione,
218. 9α-fluoro-16α,17α-isopropylidenedioxy-1,4-pregnadiene-11β,21-diol-3,20-dione,
219. 6α-fluoro-1,4-pregnadiene-11β,16α,17α,21-tetrol-3,20-dione,
220. 6α,9α-difluoro-1,4-pregnadiene-11β,16α,17α,21-tetrol-3,20-dione,
221. 6α-fluoro-1,4-pregnadiene-11β,16α,17α,21-tetrol-3,20-dione 16-acetate,
222. 6α,9α-difluoro-1,4-pregnadiene-11β,16α,17α,21-tetrol-3,20-dione 16-acetate,
223. 6α-fluoro-16α,17α-isopropylidenedioxy-1,4-pregnadiene-11β,21-diol-3,20-dione,
224. 6α,9α-difluoro-16α,17α-isopropylidenedioxy-1,4-pregnadiene-11β,21-diol-3,20-dione,
225. 6β-fluoro-1,4-pregnadiene-11β,17α,21-triol-3,20-dione,
226. 6β,9α-difluoro-1,4-pregnadiene-11β,17α,21-triol-3,20-dione,
227. 6β-fluoro-16α-methyl-1,4-pregnadiene-11β,17α,21-triol-3,20-dione,
228. 6β,9α-difluoro-16α-methyl-1,4-pregnadiene-11β,17α,21-triol-3,20-dione,
229. 6β-fluoro-16β-methyl-1,4-pregnadiene-11β,17α,21-triol-3,20-dione,
230. 6β,9α-difluoro-16β-methyl-1,4-pregnadiene-11β,17α,21-triol-3,20-dione,
231. 6β-fluoro-16-methylene-1,4-pregnadiene-11β,17α,21-triol-3,20-dione,
232. 6β,9α-difluoro-16-methylene-1,4-pregnadiene-11β,17α,21-triol-3,20-dione,
233. 2'-phenyl-11β,17α,21-trihydroxy-20-keto-4,6-pregnadieno-[3,2-c]pyrazole,
234. 2'-phenyl-6-azido-11β,17α,21-trihydroxy-20-keto-4,6-pregnadieno[3,2-c]pyrazole,
235. 2'-phenyl-6-methyl-11β,17α,21-trihydroxy-20-keto-4,6-pregnadieno[3,2-c]pyrazole,
236. 2'-phenyl-6-fluoro-11β,17α,21-trihydroxy-20-keto-4,6-pregnadieno[3,2-c]pyrazole,
237. 2'-phenyl-11β,17α,21-trihydroxy-16α-methyl-20-keto-4,6-pregnadieno[3,2-c]pyrazole,
238. 2'-phenyl-6-azido-11β,17α,21-trihydroxy-16α-methyl-20-keto-4,6-pregnadieno[3,2-c]pyrazole,
239. 2'-phenyl-6-methyl-11β,17α,21-trihydroxy-16α-methyl-20-keto-4,6-pregnadieno[3,2-c]pyrazole,
240. 2'-phenyl-6-fluoro-11β,17α,21-trihydroxy-16α-methyl-20-keto-4,6-pregnadieno[3,2-c]pyrazole,
241. 2'-phenyl-11β,17α,21-trihydroxy-16β-methyl-20-keto-4,6-pregnadieno[3,2-c]pyrazole,
242. 2'-phenyl-6-azido-11β,17α,21-trihydroxy-16β-methyl-20-keto-4,6-pregnadieno[3,2-c]pyrazole,
243. 2'-phenyl-6-methyl-11β,17α,21-trihydroxy-16β-methyl-20-keto-4,6-pregnadieno[3,2-c]pyrazole,
244. 2'-phenyl-6-fluoro-11β,17α,21-trihydroxy-16β-methyl-20-keto-4,6-pregnadieno[3,2-c]pyrazole,
245. 6-fluoro-16α-methyl-1,4,6-pregnatriene-11β,21-diol-3,20-dione,
246. 6α-fluoro-9α-chloro-16α-methyl-1,4-pregnadiene-11β,21-diol-3,20-dione,
247. 6α-fluoro-9α,11β-dichloro-16α,17α-isopropylidenedioxy-1,4-pregnadiene-21-ol-3,20-dione,
248. 6,16-dimethyl-1,4,6,15-pregnatetraene-11β,17α,21-triol-3,20-dione,
249. 16β-methyl-1,4,8-pregnatriene-11β,17α,21-triol-3,20-dione 17-propionate,
250. 9α-fluoro-[17α,16α-d]-oxazolino-1,4-pregnadiene-11β,21-diol-3,20-dione,
251. 3-(β-chloroethoxy)-6-formyl-9α-fluoro-16α,17α-isopropylidenedioxy-3,5-pregnadiene-11β,21-diol-20-one, 252. 2α-methyl-6-fluoro-4,6-pregnadiene-11β,16α,17α,21-tetrol-3,20-dione,
253. 2α-methyl-6,9α-difluoro-4,6-pregnadiene-11β,16α,17α,21-tetrol-3,20-dione,
254. 17α-chloro-1,4-pregnadiene-11β,21-diol-3,20-dione,
255. 6α-methyl-4-pregnene-11β,17α,21-triol-3,20-dione,
256. 6α-methyl-1,4-pregnadiene-11β,17α,21-triol-3,20-dione,
257. 6α,16α-dimethyl-4-pregnene-11β,17α,21-triol-3,20-dione,
258. 6α,16β-dimethyl-4-pregnene-11β,17α,21-triol-3,20-dione,
259. 6α,16α-dimethyl-1,4-pregnadiene-11β,17α,21-triol-3,20-dione,
260. 6α,16β-dimethyl-1,4-pregnadiene-11β,17α,21-triol-3,20-dione,
261. 6α-methyl-9α-fluoro-4-pregnene-11β,17α,21-triol-3,20-dione,
262. 6α-methyl-9α-fluoro-1,4-pregnadiene-11β,17α,21-triol-3,20-dione,
263. 6α,16α-dimethyl-9α-fluoro-4-pregnene-11β,17α,21-triol-3,20-dione,
264. 6α,16β-dimethyl-9α-fluoro-4-pregnene-11β,17α,21-triol-3,20-dione,
265. 6α,16α-dimethyl-9α-fluoro-1,4-pregnadiene-11β,17α,21-triol-3,20-dione,
266. 6α,16β-dimethyl-9α-fluoro-1,4-pregnadiene-11β,17α,21-triol-3,20-dione.

B. 4-Pregnene-17α,21-Diol-3,20-Dione 17-Retinoates.

In a manner similar to that described in Example 5A treat each of the 4-pregnene-17α,21-diol-3,20-dione 21-retinoates prepared in Example 13A (i.e. the 21-retinoates of starting compounds 1–186 and 211–216, 219–222, 225–244, 248 and 255–266) with cuprous iodide and methyl lithium in dry tetrahydrofuran, then isolate and purify the resultant product in a manner similar to that described to obtain the corresponding 4-pregnene-17α,21-diol-3,20-dione 17-retinoates.

C. 4-Pregnene-17α,21-Diol-3,20-Dione 17,21-Diretinoate.

In a manner similar to that described in Example 6A treat each of the 4-pregnene-17α,21-diol-3,20-dione 17-retinoates prepared as described in Example 13B with N-retinoylimidazole and sodium methoxide under an atmosphere of nitrogen in the dark. Isolate and purify each of the resultant products in a manner similar to that described to obtain 4-pregnene-17α,21-diol-3,20-dione 17,21-diretinoates, respectively.

EXAMPLE 14

TOPICAL PHARMACEUTICAL COMPOSITIONS OF STEROIDAL RETINOATES

A. Creams
(1) Hydrocortisone 21-Retinoate (0.1%)
(4-Pregnene-11β,17α,21-Triol-3,20-Dione 21-Retinoate)

| | mg/g |
|---|---|
| Hydrocortisone 21-retinoate | 1.0 |
| White Petrolatum, USP | 150.0 |
| Mineral Oil, USP | 60.0 |
| Cetylstearyl Alcohol | 72.0 |
| Cetomacrogol 1000 | 22.5 |
| 4-Chloro-m-cresol | 1.0 |
| Purified Water USP to make | 1.0g |

(2) Dexamethasone 21-Retinoate (0.25%)
(9α-Fluoro-16α-Methyl-1,4-Pregnadiene-11β,17α,21-Triol-3,20-Dione 21-Retinoate)

| | mg/g |
|---|---|
| Dexamethasone 21-retinoate | 2.5 |
| Stearyl Alcohol USP | 90.0 |
| White Petrolatum USP | 10.0 |

EXAMPLE 14-continued

TOPICAL PHARMACEUTICAL COMPOSITIONS OF STEROIDAL RETINOATES

| | |
|---|---|
| Propylene Glycol USP | 50.0 |
| Sodium Lauryl Sulfate USP | 10.0 |
| 4-Chloro-m-cresol | 1.0 |
| Purified Water USP to make | 1.0g |

(3) Betamethasone 17-Valerate 21-Retinoate (0.5%)
(9α-Fluoro-16β-Methyl-1,4-Pregnadiene-11β,17α,21-Triol-3,20-Dione 17-Valerate 21-Retinoate)

| | mg/g |
|---|---|
| Betamethasone 17 valerate 21-retinoate | 5.0 |
| Sorbitan Monostearate | 20.0 |
| Polysorbate 60 | 15.0 |
| Spermaceti USP | 30.0 |
| Cetostearyl Alcohol | 100.0 |
| 2-octyl-dodecanol | 100.0 |
| Benzyl Alcohol | 10.0 |
| Purified Water USP to make | 1.0g |

B. Ointments
(1) Hydrocortisone 21-Retinoate (0.25%)

| | mg/g |
|---|---|
| Hydrocortisone 21-retinoate | 2.5 |
| Mineral Oil USP | 50.0 |
| Propylene Glycol USP | 50.0 |
| Petrolatum USP to make | 1.0g |

(2) Hydrocortisone 21-Retinoate (0.025%)

| | mg/g |
|---|---|
| Hydrocortisone 21-retinoate | 0.25 |
| Polyethylene Glycol 400 USP | 50.00 |
| Polyethylene Glycol 4000 USP to make | 1.0g |

(3) Betamethasone 21-Retinoate (0.25%)
(9α-Fluoro-16β-Methyl-1,4-Pregnadiene-11β,17α,21-Triol-3,20-Dione 21-Retinoate)

| | mg/g |
|---|---|
| Betamethasone 21-retinoate | 2.5 |
| Hydrogenated Lanolin | 100.0 |
| Mineral Oil USP | 100.0 |
| Propylene Glycol USP | 50.0 |
| Petrolatum USP to make | 1.0g |

C. Solutions
(1) Hydrocortisone 21-Retinoate (0.1%)

| | mg/ml |
|---|---|
| Hydrocortisone 21-retinoate | 1.0 |
| Alcohol USP | 50.0 |
| Propylene Glycol USP to make | 1.0g |

(2) Dexamethasone 21-retinoate (0.5%)

| | mg/g |
|---|---|
| Dexamethasone 21-retinoate | 5.0 |
| Polyethylene Glycol 400, USP to make | 1.0g |

(3) Prednisolone 21-Retinoate (0.25%)
(1,4-Pregnadiene-11β,17α,21-Triol-3,20-Dione 21-Retinoate

| | mg/ml |
|---|---|
| Prednisolone 21-retinoate | 2.5 |
| Isopropyl Alcohol NF | 700.0 |
| Purified Water USP to make | 1.0ml |

D. Lotions
(1) Hydrocortisone 21-Retinoate (0.1%)

| | mg/g |
|---|---|
| Hydrocortisone 21-retinoate | 1.0 |
| Isopropyl Alcohol NF | 500.0 |
| Carbopol 934 | 3.0 |
| Sodium Hydroxide USP q.s. | |
| Purified Water to make | 1.0g |

E. Gels
(1) Betamethasone 17-Valerate 21-Retinoate (0.25%)

| | mg/g |
|---|---|
| Betamethasone 17-valerate 21-retinoate | 2.5 |
| Alcohol USP | 600.0 |
| Carbopol 940 | 1.0 |
| Monoisopropanolamine | 0.1 |
| Purified Water USP to make | 1.0g |

(2) Hydrocortisone 21-Retinoate (0.025%)

| | mg/g |
|---|---|
| Hydrocortisone 21-retinoate | 0.25 |
| Alcohol USP | 150.00 |
| Carbopol 940 | 30.00 |
| Propylene Glycol USP | 150.00 |
| Diisopropanolamine sufficient | |
| Purified Water USP to make | 1.0g |

EXAMPLE 15

INTRALESIONAL PHARMACEUTICAL COMPOSITIONS OF STEROIDAL RETINOATES

A. Hydrocortisone 21-Retinoate (0.1% to 0.5%)
(1)

| | mg/ml |
|---|---|
| Hydrocortisone 21-retinoate (sterile precipitated) | 1.0–5.0 |

EXAMPLE 15-continued

INTRALESIONAL PHARMACEUTICAL COMPOSITIONS OF STEROIDAL RETINOATES

| | |
|---|---|
| Monobasic Sodium Phosphate | 6.0 |
| Dibasic Sodium Phosphate Anhydrous | 0.5 |
| Polysorbate 80, USP | 0.1 |
| Benzyl Alcohol, R | 9.0 |
| Sodium Chloride, USP | 2.5 |
| Methylparaben, USP | 1.3 |
| Propylparaben, USP | 0.2 |
| Sodium Carboxymethylcellulose, USP | 3.0 |
| Disodium Edetate, USP | 0.1 |
| Water for Injection, USP q.s. ad | 1.0ml |

(2)

| | mg/ml |
|---|---|
| Hydrocortisone 21-retinoate (sterile precipitated) | 1.0–5.0 |
| Polysorbate 80 USP | 1.0 |
| Benzyl Alcohol, R | 9.0 |
| Sorbitol 70% USP | 0.5ml |
| Triethanolamine 98% USP | 7.6 |
| Hydrochloric Acid 37% | 0.0035ml |
| Water for Injection q.s. ad | 1.0ml |

B. Prednisolone 21-Retinoate (0.1% to 0.5%)

| | mg/ml |
|---|---|
| Prednisolone 21-retinoate (sterile precipitated) | 1.0–5.0 |
| Monobasic Sodium Phosphate | 6.0 |
| Dibasic Sodium Phosphate Anhydrous | 0.5 |
| Polysorbate 80, USP | 0.1 |
| Benzyl Alcohol, R | 9.0 |
| Sodium Chloride, USP | 2.5 |
| Methylparaben, USP | 1.3 |
| Propylparaben, USP | 0.2 |
| Sodium Carboxymethylcellulose, USP | 3.0 |
| Disodium Edetate, USP | 0.1 |
| Water for Injection, USP q.s. ad | 1.0ml |

C. Dexamethasone 21-Retinoate (0.25% to 0.5%)

| | mg/ml |
|---|---|
| Dexamethasone 21-retinoate (sterile precipitated) | 2.5–5.0 |
| Monobasic Sodium Phosphate | 6.0 |
| Dibasic Sodium Phosphate Anhydrous | 0.5 |
| Polysorbate 80, USP | 0.5 |
| Benzyl Alcohol, R | 9.0 |
| Methylparaben, USP | 1.3 |
| Propylparaben, USP | 0.2 |
| Sodium Chloride, USP | 2.5 |
| Sodium Carboxymethylcellulose, USP | 3.0 |
| Disodium Edetate, USP | 0.1 |
| Water for Injection, USP w.s. ad | 1.0ml |

D. Betamethasone 17-Valerate 21-Retinoate (0.25% to 0.5%)

| | mg/ml |
|---|---|
| Betamethasone 17-valerate 21-retinoate (sterile precipitated) | 2.5–5.0 |
| Monobasic Sodium Phosphate | 6.0 |
| Dibasic Sodium Phosphate Anhydrous | 0.5 |
| Polysorbate 80, USP | 0.1 |
| Benzyl Alcohol, R | 9.0 |
| Sodium Chloride, USP | 2.5 |
| Methylparaben, USP | 1.3 |
| Propylparaben, USP | 0.2 |
| Sodium Carboxymethylcellulose, USP | 3.0 |
| Disodium Edetate, USP | 0.1 |
| Water for Injection, USP q.s. ad | 1.0ml |

EXAMPLE 16

4-PREGNENE-11β,17α,21-TRIOL-3,20-DIONE 21-9,10-CIS-RETINOATE AND THE 1-DEHYDRO ANALOG THEREOF

In a manner similar to that described in Example 1A(1) treat each of 4-pregnene-11β,17α,21-triol-3,20-dione and 1,4-pregnadiene-11β,17α,21-triol-3,20-dione in dry tetrahydrofuran under nitrogen and in the dark with N-(9,10-cis-retinoyl)imidazole and sodium methoxide. Isolate and purify each of the resultant products in a manner similar to that described in Example 1A(1) to obtain 4-pregnene-11β,17α,21-triol-3,20-dione-21-9,10-cis-retinoate and 1,4-pregnadiene-11β,17α,21-triol-3,20-dione-21-9,10-cis-retinoate, respectively.

We claim:

1. A retinoic acid ester of a steroid of the pregnane series having anti-inflammatory activity and having a 20-ketone and a 3-keto-4-dehydro system or an enol ether thereof or a 3-desoxy-[3,2-c]-pyrazole derivative thereof, and also having a hydroxyl group on at least one of positions 21, 17α and 16α with the proviso that on at least one of positions 17α and 21 there is a hydroxyl group or a hydrolyzable derivative thereof; said retinoic acid ester being a member selected from the group consisting of a 21-retinoate, 17α-retinoate, 16α-retinoate, 16α,21-diretinoate and a 17α,21-diretinoate of said steroid of the pregnane series.

2. A compound of claim 1 which is an all-trans-retinoic acid ester of said steroid of the pregnane series.

3. A compound of claim 2 which is a 21-all-trans-retinoate of said steroid of the pregnane series.

4. A compound of claim 2 which is a member selected from the group consisting of a 21-all-trans-retinoate, a 17α-all-trans-retinoate, a 16α-all-trans-retinoate, a 16α,21-di-all-trans-retinoate, and a 17α,21-di-all-trans-retinoate of a member selected from the group consisting of a 3,20-diketo-4-dehydro pregnane of the following formula:

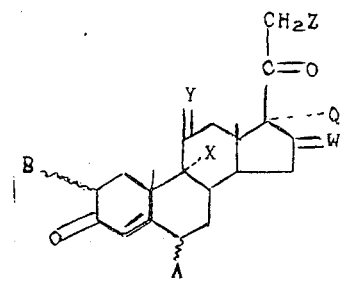

wherein A is a member selected from the group consisting of hydrogen, α-methyl, α-azido, α-bromo, α-chloro, α-fluoro, β-fluoro, and α-fluoromethyl;

B is a member selected from the group consisting of hydrogen, and when Y is (H,β-OH), methyl, fluorine, chlorine and bromine;

Q is a member selected from the group consisting of hydroxy, OR wherein R is an acyl radical of a hydrocarboncarboxylic acid having up to 12 carbon atoms, hydrogen provided W is hydrogen or (H, lower alkyl), and chlorine provided W is hydrogen or (H, lower alkyl), W is a member selected from the group consisting of $$\diagdown_H^H,$$

(H, lower alkyl), (H,α-Cl), (H,α-OH), (H,α-OR$_1$), wherein R$_1$ is an acyl radical of a hydrocarboncarboxylic acid having up to 12 carbon atoms, =CHT wherein T is a member selected from the group consisting of hydrogen, lower alkyl, fluorine and chlorine, and W and Q taken together is 16α,17α-lower alkylidenedioxy;

X is a member selected from the group consisting of hydrogen and halogen having an atomic weight of less than 100;

Y is a member selected from the group consisting of oxygen provided B is hydrogen, (H,β-OH), and (H,β-halogen) provided X is halogen; and Z is a member selected from the group consisting of hydroxy; and provided Q is hydroxy, Z is also hydrogen, chlorine, fluorine, and $OR_2$ wherein $R_2$ is an acyl radical of a hydrocarboncarboxylic acid having up to 12 carbon atoms;

and the 1-dehydro, 6-dehydro, and 1,6-bis-dehydro analogs thereof;

and when B is hydrogen, the 3-desoxy-[3,2-c]-pyrazole derivatives and the 6-dehydro analogs thereof;

and the 6,6-difluoro analogs of compounds of Formula I wherein A is hydrogen, and the 1-dehydro analogs thereof.

5. A compound of claim 4 which is a member selected from the group consisting of a steroidal 21-all-trans-retinoate ester having the following structural formula:

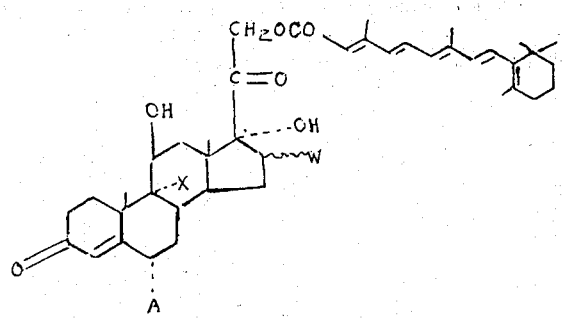

wherein A is hydrogen, methyl or fluorine; X is hydrogen or fluorine; W is hydrogen, α-methyl, β-methyl, α-hydroxy;

and the 1-dehydro, 6-dehydro, and 1,6-bis-dehydro analogs thereof.

6. A compound of claim 5 wherein at least one of X and W is hydrogen.

7. A compound of claim 5 wherein A, X and W are hydrogen, said compound being 4-pregnene-11β,17α,21-triol-3,20-dione 21-all-trans-retinoate.

8. A 1-dehydro compound of claim 5 wherein A, X and W are hydrogen, said compound being 1,4-pregnadiene-11β,17α,21-triol-3,20-dione 21-all-trans-retinoate.

9. A 1-dehydro compound according to claim 5 wherein A is hydrogen, X is fluorine and W is methyl, said compound being 9α-fluoro-16-methyl-1,4-pregnadiene-11β,17α,21-triol-3,20-dione 21-all-trans-retinoate.

10. A 16α-methyl compound of claim 9 which is 9α-fluoro-16α-methyl-1,4-pregnadiene-11β,17α,21-triol-3,20-dione 21-all-trans-retinoate.

11. A compound of claim 4 which is a 16α-all-trans-retinoate of a 1-dehydro analog of a 3,20-diketo-4-dehydro pregnane of the formula therein wherein A and B are hydrogen, W is (H,α-OH), Y is (H,β-OH) and Q is hydroxyl, X is fluorine, and Z is acetoxy, said compound being 9α-fluoro-1,4-pregnadiene-11β,16α,17α,21-tetrol-3,20-dione 16-all-trans-retinoate 21-acetate.

12. A compound of claim 4 which is a 17α-all-trans-retinoate of a 1-dehydro analog of a 3,20-diketo-4-dehydro pregnane of the formula therein wherein A and B are hydrogen, W is (H,α-methyl), X is fluorine, Y is (H,β-OH), Q and Z are hydroxy, said compound being 9α-fluoro-16α-methyl-1,4-pregnadiene-11β,17α,21-triol-3,20-dione 17-all-trans-retinoate.

13. A compound of claim 4 which is a 17α-all-trans-retinoate of a 3,20-diketo-4-dehydro pregnane of the formula therein wherein A, B, X and W are hydrogen, and Y is (H,β-OH), Q and Z are hydroxyl, said compound being 4-pregnene-11β,17α,21-triol-3,20-dione 17-all-trans-retinoate.

14. The method of treating and controlling acne which comprises applying either topically or intralesionally to the affected area in a concentration effective for the treatment of acne, a steroidal retinoate ester selected from the group consisting of a 21-retinoate, a 17α-retinoate, a 16α-retinoate, a 16α,21-diretinoate and a 17α,21-diretinoate ester of a steroid of the pregnane series, said steroid having anti-inflammatory activity and having a 20-ketone and a 3-keto-4-dehydro system or an enol ether thereof or a 3-desoxy-[3,2-c]pyrazole derivative thereof, and also having a hydroxyl group on at least none of positions 21, 17α and 16α with the proviso that on at least one of positions 17α and 21 there is a hydroxyl group or a hydrolyzable derivative thereof, together with a non-toxic, pharmaceutically acceptable carrier.

15. The method of claim 14 wherein said steroidal retinoate ester is an all-trans-retinoic acid ester of said steroid of the pregnane series.

16. The method of claim 14 when carried out via the topical route and wherein steroidal retinoate ester is an all-trans-retinoic acid ester of said steroid of the pregnane series.

17. The method of claim 16 wherein said steroidal retinoate ester is a steroidal 21-all-trans-retinoate ester.

18. The method of claim 16 wherein said steroidal retinoate ester is a 21-all-trans-retinoate defined by claim 6.

19. The method of claim 16 wherein said steroidal retinoate ester is 4-pregnene-11β,17α,21-triol-3,20-dione 21-all-trans-retinoate.

20. The method of claim 16 wherein said steroidal retinoate is 1,4-pregnadiene-11β,17α,21-triol-3,20-dione 21-all-trans-retinoate.

21. A pharmaceutical composition comprising an anti-acne effective amount of a steroidal retinoate ester selected from the group consisting of a 21-retinoate, a 17α-retinoate, a 16α-retinoate, a 16α,21-diretinoate and a 17α,21-diretinoate of a steroid of the pregnane series, said steroid having anti-inflammatory activity and having a 20-ketone and a 3-keto-4-dehydro system or an enol ether thereof or a 3-desoxy-[3,2-c]-pyrazole derivative thereof, and also having a hydroxyl group on at least one of positions 21, 17α and 16α with the proviso that on at least one of positions 17α and 21 there is a hydroxyl group or a hydrolyzable derivative thereof, together with a non-toxic, pharmaceutically acceptable carrier.

22. The composition of claim 21 wherein said steroidal retinoate ester is an all-trans-retinoic acid ester of said steroid of the pregnane series.

23. The composition of claim 22 wherein said steroidal retinoate ester is a steroidal 21-all-trans-retinoate.

24. The composition of claim 22 wherein said steroidal retinoate ester is a steroidal 21-all-trans-retinoate defined by claim 6.

25. The composition of claim 22 wherein said steroidal retinoate ester is 4-pregnene-11β,17α,21-triol-3,20-dione 21-all-trans-retinoate.

* * * * *

UNITED STATES PATENT OFFICE
CERTIFICATE OF CORRECTION

Patent No. 3,984,544   Dated October 5, 1976

Inventor(s) Charles J. Casmer et al

It is certified that error appears in the above-identified patent and that said Letters Patent are hereby corrected as shown below:

Column 4, line 65, "isoporpyli-" should read ---isopropyli--. Column 5, line 49, "combine" should read ---combined--, line 70, "-11$\alpha$,21-" should read ---11$\beta$,21---. Column 8, line 41, "diretionate" should read ---diretinoate---. Column 9, line 44, "Areas treaded" should read ---Areas treated---. Column 15, line 49, "by this" should read ---by thin---; line 51, "-11$\beta$,17$\alpha$,21-dione-" should read ---11$\beta$,17$\alpha$,21-triol-3,20-dione---; line 64, "-Diretionate." should read ---Diretinoate.---. Column 16, line 40, "-3,30-Dione-" should read ---3,20-Dione---. Column 17, line 55, "with ethly-" should read ---with ethyl---. Column 20, line 3, "11$\alpha$,21-difluoro-" should read ---11$\beta$,21-difluoro---. Column 22, line 20, "-11$\alpha$,17$\alpha$-" should read ---11$\beta$,17$\alpha$---. Column 24, line 33, "4-pregnadiene-" should read ---4-pregnene---; line 35, "-6$\alpha$,9$\alpha$-difluoro-" should read ---6$\alpha$-fluoro---. Column 26, line 41, "-6-azido-9$\alpha$-methyl-" should read ---6-azido-9$\alpha$-chloro-16$\alpha$-methyl---. Column 27, line 52, "-3,11,10-trione," should read ---3,11,20-trione,---. Column 28, line 7, "60$\alpha$-methyl" should read ---16$\alpha$-methyl---. Column 28, line 13, "-16$\alpha$-methyl-" should read ---16$\beta$-methyl---; line 66, "-17$\beta$,21-" should read ---17$\alpha$,21---. Column 29, line 36, "-11$\alpha$,21-" should read ---11$\beta$,21---; line 49, "-16$\alpha$-methyl-" should read ---16$\beta$-methyl---; line 51, "-11$\alpha$,21-" should read ---11$\beta$,21---. Column 30, line 31, "-pregnadiene[3,2-c]-" should read ---pregnadieno[3,2-c]---. Column 36, line 20, "none of" should read ---one of---.

Signed and Sealed this

Twenty-second Day of February 1977

[SEAL]

Attest:

RUTH C. MASON  
Attesting Officer

C. MARSHALL DANN  
Commissioner of Patents and Trademarks